United States Patent
Riedel et al.

(10) Patent No.: US 10,195,598 B2
(45) Date of Patent: Feb. 5, 2019

(54) PROCESS FOR THE REGENERATION OF A TITANIUM ZEOLITE CATALYST FOR PROPYLENE EPOXIDATION

(71) Applicants: BASF SE, Ludwigshafen (DE); Dow Global Technologies LLC, Midland, MI (US)

(72) Inventors: Dominic Riedel, Lampertheim (DE); Joaquim Henrique Teles, Waldsee (DE); Daniel Urbanczyk, Griesheim (DE); Ulrike Wegerle, Worms (DE); Luise Spiske, Seeheim-Jugenheim (DE); Andrei-Nicolae Parvulescu, Ruppertsberg (DE); Alexander Schroeder, Wattenheim (DE); Ulrich Mueller, Neustadt (DE); Meinolf Weidenbach, Stade (DE); Werner J. Witzl, Stade (DE)

(73) Assignees: BASF SE, Ludwigshafen (DE); Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/550,581

(22) PCT Filed: Feb. 12, 2016

(86) PCT No.: PCT/EP2016/052983
§ 371 (c)(1),
(2) Date: Aug. 11, 2017

(87) PCT Pub. No.: WO2016/128538
PCT Pub. Date: Aug. 18, 2016

(65) Prior Publication Data
US 2018/0036723 A1    Feb. 8, 2018

Related U.S. Application Data

(60) Provisional application No. 62/115,658, filed on Feb. 13, 2015.

(30) Foreign Application Priority Data

Feb. 13, 2015 (EP) .................................. 15154998

(51) Int. Cl.
| | | |
|---|---|---|
| *B01J 29/89* | (2006.01) | |
| *B01J 38/12* | (2006.01) | |
| *B01J 38/48* | (2006.01) | |
| *B01J 29/90* | (2006.01) | |
| *B01J 35/02* | (2006.01) | |
| *B01J 35/10* | (2006.01) | |
| *C07D 301/12* | (2006.01) | |
| *C01B 39/08* | (2006.01) | |

(52) U.S. Cl.
CPC ............... *B01J 29/89* (2013.01); *B01J 29/90* (2013.01); *B01J 38/12* (2013.01); *B01J 38/48* (2013.01); *C07D 301/12* (2013.01); *B01J 35/023* (2013.01); *B01J 35/1061* (2013.01); *B01J 2229/183* (2013.01); *B01J 2229/186* (2013.01); *C01B 39/085* (2013.01); *Y02P 20/52* (2015.11); *Y02P 20/584* (2015.11)

(58) Field of Classification Search
CPC ... B01J 29/89; B01J 38/48; B01J 38/12; B01J 29/90; B01J 35/023; B01J 2229/186; B01J 2229/183; B01J 35/1061; C07D 301/12; C01B 39/085; Y02P 20/584; Y02P 20/52
See application file for complete search history.

(56) References Cited

U.S. PATENT DOCUMENTS

| | | |
|---|---|---|
| 6,114,551 A | 9/2000 | Levin et al. |
| 2002/0091276 A1 | 7/2002 | Thiele et al. |
| 2003/0187286 A1 | 10/2003 | Teles et al. |
| 2005/0277542 A1 | 12/2005 | Kaminsky et al. |
| 2007/0043226 A1 | 2/2007 | Muller et al. |
| 2011/0009651 A1 | 1/2011 | Kawabata et al. |

FOREIGN PATENT DOCUMENTS

| | | |
|---|---|---|
| CN | 101480623 A | 7/2009 |
| EP | 1 221 442 A1 | 7/2002 |
| WO | WO 98/55229 A1 | 12/1998 |

(Continued)

OTHER PUBLICATIONS

Wu P., Xu H., Xu L., Liu Y., He M. (2013) Chapter 2. Synthesis of Ti-MWW Zeolite. In: MWW-Type Titanosilicate. SpringerBriefs in Molecular Science. Springer, Berlin, Heidelberg.*

(Continued)

*Primary Examiner* — John M Mauro
(74) *Attorney, Agent, or Firm* — Oblon, McClelland, Maier & Neustadt, L.L.P.

(57) ABSTRACT

The invention relates to process for the regeneration of a catalyst comprising a titanium containing zeolite as catalytically active material comprising a stage comprising introducing a feed stream comprising propene, hydrogen peroxide or a hydrogen peroxide source, and an organic solvent into a reactor containing a catalyst comprising the titanium containing zeolite, subjecting the feed stream in the reactor to epoxidation conditions in the presence of the catalyst, removing a product steam comprising propylene oxide and the organic solvent from the reactor, stopping introducing the feed stream, washing the catalyst with a liquid aqueous system and calcining the washed catalyst.

18 Claims, 2 Drawing Sheets

(56) References Cited

FOREIGN PATENT DOCUMENTS

| WO | WO 2005/000827 A1 | 1/2005 |
| WO | WO 2007/013739 A1 | 2/2007 |
| WO | WO 2013/117536 A2 | 8/2013 |
| WO | WO 2015/010994 A1 | 1/2015 |

OTHER PUBLICATIONS

Wu, P., "Unique trans-selectivity of Ti-MWW in epoxidation of cis/trans-alkenes with hydrogen peroxide." The Journal of Physical Chemistry B 106.4 (2002): 748-753.*

International Search Report dated Jun. 1, 2016 in PCT/EP2016/052983.

International Preliminary Report on Patentability dated May 16, 2017 in PCT/EP2016/052983.

A. Wróblewska, et al., "Regeneration of the Ti-SBA-15 Catalyst Used in the Process of Allyl Alcohol Epoxidation with Hydrogen Peroxide", Journal of Advanced Oxidation Technologies, vol. 17 No. 1, XP009185800, 2014, pp. 44-52.

"Ullmann's Encyclopedia of Industrial Chemistry: Fifth Edition", VCH, vol. 13, pp. 443-456 with cover page.

Ch. Baerlocher, et al., "Atlas of Zoelite Framework Types", Elsevier, 2001, 303 Pages with cover page.

Peng Wu, et al., "Hydrothermal Synthesis of a Novel Titanosilicate with MWW Topology", Chemistry Letters, 2000, pp. 774-775.

\* cited by examiner

PROCESS FOR THE REGENERATION OF A TITANIUM ZEOLITE CATALYST FOR PROPYLENE EPOXIDATION

The present invention relates to a process for the regeneration of a catalyst comprising a titanium containing zeolite as catalytically active material, to a regenerated catalyst, and a continuous process for the preparation of propylene oxide.

In the past years, various titanium-containing zeolites have been developed which are useful in catalyzing organic reactions such as the conversion of olefins to epoxides. For example, WO 98/55229 A1 discloses the production and further the use of a titanium containing zeolite for the epoxidation of olefins.

Titanium containing zeolites are of great industrial interest, and in this context economical and environmental considerations are of significant relevance. An efficient regeneration of such zeolites for subsequent re-use in the catalysis of organic reactions would be strongly preferred over their replacement with fresh catalyst.

EP 1 221 442 A1 discloses the regeneration of a titanium zeolite catalyst used in the epoxidation of olefins with hydrogen peroxide, the process comprising performing the epoxidation reaction, wherein the regeneration of the spent catalyst is carried out with hydrogen peroxide in the presence of the olefin whereby the epoxidation reaction is continued and wherein the regeneration is achieved by reversal of the feed direction of the hydrogen peroxide. Hydrogen peroxide is also a valuable starting material and as such difficult to handle due to its tendency to decompose spontaneously.

WO 2005/000827 A1 discloses the regeneration of a titanium silicalite catalyst following a process for the continuous epoxidation of propene with hydrogen peroxide. The catalyst is periodically regenerated with a methanol solvent at a temperature of at least 100° C. Methanol is a valuable organic compound which requires an expensive and time consuming recovery. After regeneration, the epoxidation has to be restarted at a higher temperature compared with the fresh catalyst in the WO 2005/000827 A1.

WO 2007/013739 A1 discloses the regeneration of a titanium containing molecular sieve catalyst wherein, after a pretreatment of the spent catalyst with water or alcohol, the thus pretreated catalyst is brought into contact with a mixture which comprises hydrogen peroxide, water, and alcohol. This process thus includes two mandatory and subsequent steps in which the spent catalyst is brought into contact with two different solutions. Additionally, work-up of the mixture comprising hydrogen peroxide, water, and alcohol is required.

Therefore, it was an object of the present invention to provide a simple and cost-effective process for the regeneration of a catalyst comprising a titanium containing zeolite as catalytically active material used in the epoxidation of olefins. It was a further object of the present invention to provide a regenerated catalyst comprising a titanium containing zeolite as catalytically active material which may be readily re-used in the epoxidation of olefins.

Thus, the present invention relates to a process for the regeneration of a catalyst comprising a titanium containing zeolite as catalytically active material, comprising
(i) a stage comprising
  (a) continuously preparing propylene oxide comprising
    (a1) introducing a feed stream comprising propene, hydrogen peroxide or a hydrogen peroxide source, and an organic solvent into a reactor containing a catalyst comprising the titanium containing zeolite as catalytically active material;
    (a2) subjecting the feed stream according to (a1) in the reactor to epoxidation conditions in the presence of the catalyst, obtaining a reaction mixture comprising the propylene oxide and the organic solvent;
    (a3) removing a product stream comprising the propylene oxide and the organic solvent from the reactor;
  (b) stopping introducing the feed stream into the reactor;
  (c) washing the catalyst with a liquid aqueous system;
  stage (i) further comprising repeating the sequence of steps (a) to (c) n times with n being an integer and being at least 1; the process for the regeneration further comprising
(ii) a stage comprising calcining the catalyst obtained from (c) after having repeated the sequence of steps (a) to (c) n times;
wherein the sequence of stages (i) to (ii) is optionally repeated m times with m being an integer and being at least 1, wherein in each repetition of the sequence of stages (i) to (ii), n is the same or different.

Surprisingly, according to the process according to the present invention, the regeneration of a catalyst comprising a titanium containing zeolite as catalytically active material used in an epoxidation of olefins can be accomplished by washing the catalyst with a liquid aqueous system according to step (c) of stage (i) at least once without subsequent calcination, wherein after said washing, the catalyst exhibits the same or at least substantially the same catalytic activity as the respective fresh catalyst already without a calcination step, and wherein the results of the regeneration can even be enhanced by the calcining the catalyst according to stage (ii) after one or more further washing steps.

Stage (i)

Stage (i) of the present process comprises
(a) continuously preparing propylene oxide comprising
  (a1) introducing a feed stream comprising propene, hydrogen peroxide or a hydrogen peroxide source, and an organic solvent into a reactor containing a catalyst comprising the titanium containing zeolite as catalytically active material;
  (a2) subjecting the feed stream according to (a1) in the reactor to epoxidation conditions in the presence of the catalyst, obtaining a reaction mixture comprising the propylene oxide and the organic solvent;
  (a3) removing a product stream comprising the propylene oxide and the organic solvent from the reactor;
(b) stopping introducing the feed stream into the reactor;
(c) washing the catalyst with a liquid aqueous system;
stage (i) further comprising repeating the sequence of steps (a) to (c) n times with n being an integer and being at least 1.

Step (a1)

The feed stream according to (a1) comprises propene, hydrogen peroxide or a hydrogen peroxide source, and an organic solvent.

Hydrogen Peroxide or Hydrogen Peroxide Source

Both hydrogen peroxide and a hydrogen peroxide source may be employed as an epoxidation agent in the feed steam according to (a1).

In case that hydrogen peroxide is employed, it is preferred that the hydrogen peroxide is an aqueous hydrogen peroxide solution, wherein the solution comprises preferably 30 to 50 weight-% hydrogen peroxide relative to the total amount of water.

It is also possible that the hydrogen peroxide is formed in situ in the reaction mixture from hydrogen and oxygen in the presence of a suitable catalyst or catalyst system, for example in the presence of a titanium containing zeolite additionally containing one or more noble metals, or a titanium containing zeolite and an additional catalyst containing one or more noble metals, for example supported on a suitable support such as charcoal or a suitable inorganic oxide or mixture of inorganic oxides.

For the preparation of the hydrogen peroxide in the feed stream according to (a1) the anthraquinone process may be used. This process is based on the catalytic hydrogenation of an anthraquinone compound to form the corresponding anthrahydroquinone compound, subsequent reaction of this with oxygen to form hydrogen peroxide and subsequent extraction of the hydrogen peroxide formed. The cycle is completed by re-hydrogenation of the anthraquinone compound which has been formed again in the oxidation. A review of the anthraquinone process is given in "Ullmann's Encyclopedia of Industrial Chemistry", 5th edition, volume 13, pages 447 to 456. As an alternative, the hydrogen peroxide may be obtained by anodic oxidation of sulfuric acid with simultaneous evolution of hydrogen at the cathode to produce peroxodisulfuric acid. Hydrolysis of the peroxodisulfuric acid forms firstly peroxosulfuric acid and then hydrogen peroxide and sulfuric acid, which is thus recovered. In a further alternative, the hydrogen peroxide may be obtained directly from the elements hydrogen and oxygen.

Preferably, hydrogen peroxide is used in the feed stream according to (a1).

Organic Solvent

Organic solvents to be employed in (a1) are in principle all solvents known for this purpose. Preference is given to organic solvents such as alcohols, nitriles, and mixtures thereof, optionally also water. Preferably, the organic solvent is selected from the group consisting of methanol and acetonitrile. More preferably, the organic solvent is acetonitrile.

Feed Stream According to (a1)

Generally, the feed stream according to (a1) can be prepared according to any conceivable method. Thus, the feed stream in (a1) may be prepared by mixing a stream comprising the propene, a stream comprising the hydrogen peroxide or the hydrogen peroxide source, and a stream comprising the organic solvent, which encompasses a sequential mixing, i.e., mixing of a stream comprising the propene with a stream comprising the organic solvent and mixing of the resulting stream with a stream comprising the hydrogen peroxide or the hydrogen peroxide source.

Generally, the feed stream according to (a1) is not restricted regarding the molar ratio of propene and hydrogen peroxide or one equivalent of hydrogen peroxide resulting from the hydrogen peroxide source. Preferably, propene is present in a molar excess in the feed stream according to (a1) with regard to hydrogen peroxide or one equivalent of hydrogen peroxide resulting from the hydrogen peroxide source. Preferably, the molar ratio of propene and hydrogen peroxide or one equivalent of hydrogen peroxide resulting from the hydrogen peroxide source in the feed stream according to (a1) is from 1 to 1.6, more preferably from 1.1 to 1.55, more preferably from 1.2 to 1.5, more preferably from 1.40 to 1.45.

Generally, the feed stream according to (a1) comprising propene, hydrogen peroxide or a hydrogen peroxide source, and an organic solvent is not restricted regarding further components comprised by the feed stream. Thus, the feed stream according to (a1) may further comprise at least one additional component, for example at least one potassium comprising salt.

The Potassium Comprising Salt

Regarding the chemical nature of the at least one potassium salt, no specific restrictions exist. Preferably the at least one potassium salt is selected from the group consisting of at least one inorganic potassium salt, at least one organic potassium salt, and combinations of at least one inorganic potassium salt and at least one organic potassium salt.

Preferred inorganic potassium comprising salts include, but are not restricted to, potassium halides such as potassium chloride or potassium bromide, potassium nitrate, potassium sulfate, potassium hydrogen sulfate, potassium hydroxide, potassium perchlorate, potassium salts comprising phosphorus such as potassium dihydrogen phosphate or dipotassium hydrogen phosphate or potassium phosphate or potassium pyrophosphates such as monobasic potassium pyrophosphate or dibasic potassium pyrophosphate or tribasic potassium pyrophosphate or tetrabasic potassium pyrophosphate, or potassium etidronates such as monobasic potassium etidronate or dibasic potassium etidronate or tribasic potassium etidronate or tetrabasic potassium etidronate, potassium cyanate, potassium oxides such as potassium oxide ($K_2O$) or potassium superoxide ($KO_2$) or potassium peroxide ($K_2O_2$).

Preferred organic potassium comprising salts include, but are not restricted to, potassium carbonate ($K_2CO_3$), potassium hydrogen carbonate, potassium salts of aliphatic saturated carboxylic acids such as monocarboxylic acids preferably having from 1 to 6, more preferably from 1 to 5, more preferably from 1 to 4, more preferably from 1 to 3 carbon atoms such as formic acid, acetic acid, propionic acid, dicarboxylic acids preferably having from 2 to 6, more preferably from 2 to 4 carbon atoms such as oxalic acid, malonic acid, succinic acid, tartaric acid, tricarboxylic acids preferably having from 6 to 10 carbon atoms such as citric acid or isocitric acid or propane-1,2,3-tricarboxylic acid, or tetracarboxylic acids. Preferably, the organic potassium salt is selected from the group consisting of potassium salts of aliphatic saturated monocarboxylic acids preferably having 1, 2, 3, 4, 5 or 6 carbon atoms, potassium carbonate, and potassium hydrogen carbonate. More preferably, the organic potassium salt is selected from the group consisting of potassium formate, potassium acetate, potassium propionate, potassium carbonate, and potassium hydrogen carbonate. More preferably, the organic potassium salt is selected from the group consisting of potassium formate, potassium acetate, potassium carbonate, and potassium hydrogen carbonate.

Therefore, the potassium comprising salt is preferably selected from the group consisting of at least one inorganic potassium salt selected from the group consisting of potassium hydroxide, potassium halides, potassium nitrate, potassium sulfate, potassium hydrogen sulfate, potassium perchlorate, potassium dihydrogen phosphate or dipotassium hydrogen phosphate or potassium phosphate or potassium pyrophosphates such as monobasic potassium pyrophosphate or dibasic potassium pyrophosphate or tribasic potassium pyrophosphate or tetrabasic potassium pyrophosphate, or potassium etidronates such as monobasic potassium etidronate or dibasic potassium etidronate or tribasic potassium etidronate or tetrabasic potassium etidronate, at least one organic potassium salt selected from the group consisting of potassium salts of aliphatic saturated monocarboxylic acids preferably having 1, 2, 3, 4, 5 or 6 carbon atoms, potassium carbonate, and potassium hydrogen carbonate, and a combination of at least one of the at least one inorganic potassium salts and at least one of the at least one organic potassium salts.

More preferably, the potassium comprising salt is selected from the group consisting of at least one inorganic potassium salt selected from the group consisting of potassium dihydrogen phosphate or dipotassium hydrogen phosphate or potassium phosphate potassium hydroxide, potassium halides, potassium nitrate, potassium sulfate, potassium hydrogen sulfate, potassium perchlorate, at least one organic potassium salt selected from the group consisting of potassium formate, potassium acetate, potassium propionate, potassium carbonate, and potassium hydrogen carbonate, and a combination of at least one of the at least one inorganic potassium salts and at least one of the at least one organic potassium salts.

Especially preferably, the potassium comprising salt is potassium dihydrogen phosphate, dipotassium hydrogen phosphate, or potassium formate. Therefore, if one single potassium salt is employed, the potassium comprising salt is most preferably potassium dihydrogen phosphate, dipotassium hydrogen phosphate, or potassium formate. If two or more potassium comprising salts are employed, one potassium salt is potassium dihydrogen phosphate, dipotassium hydrogen phosphate, or potassium formate.

Regarding the concentration of the potassium comprising salt in the feed stream, no specific restrictions exist. Preferably, the concentration of the potassium comprising salt in feed stream is at least 10%, preferably in the range of from 10 to 100%, preferably from 20 to 100%, more preferably from 30 to 100%, more preferably from 40 to 100% of the solubility limit of the potassium comprising salt in the feed stream. The term "solubility limit of the at least one potassium salt in the liquid feed stream" as used in the context of the present invention relates to the saturation concentration of the potassium comprising salt in the liquid feed stream, where by adding more of the potassium comprising salt, the concentration of the potassium comprising salt as solute in the mixture does not increase and the potassium comprising salt would begin to precipitate. The solubility limit of the potassium comprising salt in the feed stream will depend on the composition of the mixture and the conditions such as the temperature at which, and the pressure under which the feed stream is provided. Determining the solubility limit of the potassium comprising salt in the mixture is an easy and straight-forward task for the skilled person knowing said conditions and said composition of a given mixture. A simple procedure to evaluate whether the amount of the potassium comprising salt being added is above the solubility limit is passing the feed stream before subjecting to epoxidation conditions in (a2) through a filter and measure the pressure drop across the filter. If the pressure drop across the filter increases with time on stream and the potassium comprising salt is found on the filter when it is taken offline, the amount of the potassium comprising salt being added is already above the solubility limit.

Preferably in (a1), the molar ratio of potassium comprised in the potassium comprising salt relative to hydrogen peroxide or one equivalent of hydrogen peroxide resulting from the hydrogen peroxide source comprised in the feed stream is in the range of from $10 \times 10^{-6}:1$ to $1500 \times 10^{-6}:1$, preferably from $20 \times 10^{-6}:1$ to $1300 \times 10^{-6}:1$, more preferably from $30 \times 10^{-6}:1$ to $1000 \times 10^{-6}:1$. The molar amount of the potassium comprised in the potassium comprising salt relates to the total molar amount of potassium comprised in all potassium comprising salts employed in (a1), if two or more potassium comprising salts are employed.

Further preferably in (a1), the molar ratio of potassium relative to hydrogen peroxide or one equivalent of hydrogen peroxide resulting from the hydrogen peroxide source in the feed stream is in the range of from $10 \times 10^{-6}:1$ to $5000 \times 10^{6}:1$, preferably from $15 \times 10^{-6}:1$ to $2500 \times 10^{-6}:1$, more preferably from $20 \times 10^{6}:1$ to $1,500 \times 10^{-6}:1$, more preferably from $25 \times 10^{6}:1$ to $1,300 \times 10^{-6}:1$, more preferably from $30 \times 10^{-6}:1$ to $1,000 \times 10^{-6}:1$.

Preferably, the feed stream according to (a1) is free of ammonium dihydrogen phosphate. More preferably, the feed stream according to (a1) is free of ammonium phosphate, ammonium hydrogen phosphate and ammonium dihydrogen phosphate. More preferably, the feed stream according to (a1) is free of ammonium carbonate, ammonium hydrogen carbonate, ammonium dihydrogen phosphate, ammonium hydrogen phosphate, ammonium phosphate, ammonium hydrogen pyrophosphate, ammonium pyrophosphate, ammonium chloride, ammonium nitrate, and ammonium acetate. More preferably, the feed stream according to (a1) is free of an ammonium salt. The term "free of" as used in this context relates to a concentration of a respective compound of at most 2 weight-ppm, preferably at most 1 weight-ppm, based on the total weight of the feed stream.

Preferably, the feed stream according to (a1) contains sodium in a molar ratio of sodium relative to hydrogen peroxide or one equivalent of hydrogen peroxide resulting from the hydrogen peroxide source in the range of from $1)(10^{-6}:1$ to $250 \times 10^{-6}:1$, preferably from $5 \times 10^{-6}:1$ to $50 \times 10^{-6}:1$. Preferably, the mixture, preferably the feed stream according to (a1) does not comprise dissolved sodium dihydrogen phosphate ($NaH_2PO_4$), more preferably neither dissolved sodium dihydrogen phosphate nor dissolved disodium hydrogen phosphate ($Na_2HPO_4$), more preferably neither dissolved sodium dihydrogen phosphate nor dissolved disodium hydrogen phosphate nor dissolved sodium phosphate ($Na_3PO_4$).

In case that the feed stream according to (a1) further comprises at least one potassium comprising salt, the liquid feed stream is preferably prepared by combining at least four individual streams. Preferably, an aqueous stream comprising at least one dissolved potassium comprising salt is combined with the stream comprising the propene, or with the stream comprising the hydrogen peroxide or the hydrogen peroxide source, or with the stream comprising the organic solvent, or with a mixed stream of two or three of these streams, preferably with the stream comprising the hydrogen peroxide or the hydrogen peroxide source, or with the stream comprising the organic solvent, or with a mixed stream thereof.

The stream comprising propene may additionally comprise propane, wherein preferably at least 98 weight-%, more preferably at least 99 weight-%, more preferably at least 99.5 weight-%, more preferably at least 99.9 weight-% of the stream consist of propene and propane. Preferably, the weight ratio of propene relative to propane in the stream is at least 7:3. For example, commercially available propene can be employed which may be either a polymer grade propene or a chemical grade propene. Typically, polymer grade propene has a propene content in the range of from 99 to 99.8 weight-% and a propane content in the range of from 0.2 to 1 weight-%. Chemical grade propene typically has a propene content in the range of from 92 to 98 weight-% and a propane content in the range of from 2 to 8 weight-%. Preferably, a stream is employed having a propene content in the range of from 99 to 99.8 weight-% and a propane content in the range of from 0.2 to 1 weight-%.

The stream comprising hydrogen peroxide or the hydrogen peroxide source can be prepared according to every conceivable method. It is conceivable to obtain the stream comprising hydrogen peroxide by converting sulphuric acid into peroxodisulphuric acid by anodic oxidation with simultaneous evolution of hydrogen at the cathode. Hydrolysis of the peroxodisulphuric acid then leads via peroxomonosulphuric acid to hydrogen peroxide and sulphuric acid which is thus obtained back. The preparation of hydrogen peroxide from the elements is also conceivable. Depending on the specific preparation method, the stream comprising hydrogen peroxide can be, for example, an aqueous or an aqueous/methanolic hydrogen peroxide stream, preferably an aqueous hydrogen peroxide stream. In case an aqueous hydrogen peroxide feed is employed, the content of the stream with respect to hydrogen peroxide is usually in the range of from 3 to 85 weight-%, preferably from 25 to 75 weight-%, more preferably from 30 to 50 weight-%, such as from 30 to 40 weight-% or from 35 to 45 weight-% of from 40 to 50 weight-%. Preferably, at least 25 weight-%, more preferably at least 30 weight-%, more preferably at least 35 weight-% of the stream comprising hydrogen peroxide consist of water and hydrogen peroxide. Preferred ranges are from 30 to 80 weight-% or from 35 to 75 weight-% or from 40 to 70 weight-%.

In order to provide a sufficient stability of the hydrogen peroxide during extraction with water, preferably essentially pure water, suitable stabilizing agents are usually added to the water, preferably the essentially pure water used. In particular, strong inorganic acids and/or chelating agents are to be mentioned. According to preferred extraction processes, small amounts of nitrates and/or phosphates and pyrophosphates, respectively, are added as stabilizing agents, either as acids or as sodium salts. These stabilizing agents are usually added in amounts so that the crude aqueous hydrogen peroxide solution contains from 50 to 400 weight-ppm sodium cations, from 100 to 700 weight-ppm phosphorus calculated as phosphate ($PO_4^{3-}$), and from 50 to 400 weight-ppm nitrate anions, in each case calculated with respect to hydrogen peroxide contained in the crude aqueous hydrogen peroxide solution. Preferred ranges are, for example, from 50 to 200 weight-ppm or from 50 to 100 weight-ppm of sodium cations, from 100 to 500 weight-ppm or from 100 to 300 weight-ppm of phosphorus, and 50 to 200 weight-ppm or 50 to 100 weight-ppm of nitrate. Further, it is conceivable that other stabilizing agents such as stannites like sodium stannite ($Na_2SnO_2$) and/or organic phosphonic acids, in particular organic diphosphonic acids like etidronic acid are used. Preferably, the aqueous hydrogen peroxide stream comprises sodium with a molar ratio of sodium relative to hydrogen peroxide in the range of from $1\times10^{-6}:1$ to $250\times10^{-6}:1$, more preferably from $5\times10^6:1$ to $50\times10^{-6}:1$.

Generally, the molar ratio of water relative to the organic solvent in the feed stream provided in (a1) is not subject to any specific restrictions. Preferably, in particular in case the organic solvent is acetonitrile, the molar ratio of water relative to the organic solvent is at most 1:4, more preferably in the range of from 1:50 to 1:4, preferably from 1:15 to 1:4.1, more preferably from 1:10 to 1:4.2.

Catalyst according to (a1)

Generally, the titanium containing zeolite used as catalytically active material may have a zeolitic framework structure type according to the following three-letter codes: ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITW, IWR, IWW, JBW, KFI, LAU, LEV, LIO, LOS, LOV, LTA, LTL, LTN, MAR, MAZ, MEI, MEL, MEP, MER, MMFI, MFS, MON, MOR, MSO, MTF, MTN, MTT, MTW, MWW, NAB, NAT, NEES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN SFO, SGT, SOD, SSY, STF, STI, STT, TER, THO, TON, TSC, UEI, UFI, UOZ, USI, UTL, VET, VFI, VNI, VSV, WEI, WEN, YUG, ZON, or a mixed structure of two or more of these framework structures. Regarding the three-letter codes and their definitions, reference is made to the "Atlas of Zeolite Framework Types", 5th edition, Elsevier, London, England (2001).

It is preferred that the titanium containing zeolite has an MFI framework structure, an MEL framework structure, an MWW framework structure, an MWW-type framework structure, or a mixed structure of two or more of these framework structures, preferably an MFI framework structure, an MWW framework structure or an MWW-type framework structure, more preferably an MWW framework structure or an MWW-type framework structure. More preferably, the titanium containing zeolite is a zeolite known as "TS-1" (titanium silicalite-1) or "TiMWW".

Preferably, in particular in case the titanium containing zeolite is TiMWW, the titanium containing zeolite comprises one or more of Al, B, Zr, V, Nb, Ta, Cr, Mo, W, Mn, Fe, Co, Ni, Zn, Ga, Ge, In, Sn, Pb, Pd, Pt, Au, Cd, preferably one or more of B, Zr, V, Nb, Ta, Cr, Mo, W, Mn, Fe, Co, Ni, Zn, Ga, Ge, In, Sn, Pb, Pd, Pt, Au, Cd, more preferably Zn.

The term "titanium zeolite of framework structure type MWW" as used in the context of the present invention, also referred to as "TiMWW", relates to a zeolite of framework structure MWW which contains titanium as isomorphous substitution element in the zeolitic framework. Preferably, the zeolitic framework is essentially free of aluminum and essentially consists of silicon, titanium, and oxygen. Preferably, at least 99 weight-%, more preferably at least 99.5 weight-%, more preferably at least 99.9 weight-% of the zeolitic framework consist of silicon, titanium, and oxygen. Optionally, the titanium zeolite of framework structure type MWW may comprise extra-framework titanium which is to be understood as every titanium species which is not part of the MWW zeolitic framework. The preparation of TiMWW catalysts is described, for example, in US 2007043226 A1, in particular in Examples 3 and 5 therein.

The titanium content of the titanium zeolite of framework structure type MWW is not subject to any specific restrictions. Preferably, the titanium zeolite of framework structure type MWW comprised in the catalyst in (a1) contains titanium, calculated as elemental titanium, in an amount in the range of from 0.1 to 5 weight-%, more preferably from 0.2 to 4 weight-%, more preferably from 0.5 to 3 weight-%, more preferably from 1 to 2 weight-%, based on the total weight of the titanium zeolite of framework structure type MWW. Therefore, the present invention relates to the process as described above, wherein the titanium zeolite of framework structure type MWW comprised in the catalyst in (a1) contains titanium, calculated as elemental titanium, in an amount in the range of from 0.1 to 5 weight-%, preferably from 1 to 2 weight-%, silicon, based on the total weight of the titanium zeolite of framework structure type MWW.

In addition to the titanium, the titanium zeolite of framework structure type MWW may comprise at least one further element other than titanium, silicon, and oxygen. Generally, it is conceivable that this at least one further element is an isomorphous substitution element which is part of the MWW zeolitic framework structure. Preferably, this at least one further element is not an isomorphous substitution element. Such a further element which is not an isomorphous substitution element can be applied to the zeolite by, for example, a spray process, a wet impregnation process such as an incipient wetness process, or any other suitable process. Preferably, the at least one further element is selected from the group consisting of Al, B, Zr, V, Nb, Ta, Cr, Mo, W, Mn, Fe, Co, Ni, Zn, Ga, Ge, In, Sn, Pb, Pd, Pt, Au, Cd and a combination of two or more, preferably from the group consisting of B, Zr, V, Nb, Ta, Cr, Mo, W, Mn, Fe, Co, Ni, Zn, Ga, Ge, In, Sn, Pb, Pd, Pt, Au, Cd combination of two or more. More preferably, the titanium zeolite of framework structure type MWW contains zinc as further element in addition to titanium, silicon, and oxygen. More preferably, the titanium zeolite of framework structure type MWW contains zinc as the sole further element in addition to titanium, silicon, and oxygen. More preferably, the titanium zeolite of framework structure type MWW contains zinc as the sole further element in addition to titanium, silicon, and oxygen wherein at least 99 weight-%, more preferably at least 99.5 weight-%, more preferably at least 99.9 weight-% of the zeolitic framework structure consist of silicon, titanium, and oxygen. More preferably, in case the titanium zeolite of framework structure type MWW contains zinc as the sole further element, at least 99 weight-%, more preferably at least 99.5 weight-%, more preferably at least 99.9 weight-% of the titanium zeolite of framework structure type MWW consist of zinc, titanium, silicon, and oxygen; this titanium zeolite of framework structure type MWW which contains zinc as the sole further element is also referred to as "ZnTiMWW".

ZnTiMWW Catalyst

The zinc content of the titanium zeolite of framework structure type MWW is not subject to any specific restrictions. Preferably, the titanium zeolite of framework structure type MWW comprised in the catalyst in (a1) contains zinc, calculated as elemental zinc, in an amount in the range of from 0.1 to 5 weight-%, more preferably from 0.2 to 4 weight-%, more preferably from 0.5 to 3 weight-%, more preferably from 1 to 2 weight-%, based on the total weight of the titanium zeolite of framework structure type MWW. Therefore, the present invention relates to the process as described above, wherein the titanium zeolite of framework structure type MWW comprised in the catalyst in (a1) contains zinc, calculated as elemental zinc, in an amount in the range of from 0.1 to 5 weight-%, preferably from 1 to 2 weight-%, based on the total weight of the titanium zeolite of framework structure type MWW.

Thus, it is preferred that the titanium containing zeolite which is comprised in the catalyst in (a1) has an MWW framework structure, comprises zinc, and contains titanium, calculated as elemental titanium, in an amount in the range of from 0.1 to 5 weight-%, preferably from 1 to 2 weight-%, based on the total weight of the titanium containing zeolite, and contains zinc, calculated as elemental zinc, in an amount in the range of from 0.1 to 5 weight-%, preferably from 1 to 2 weight-%, based on the total weight of the titanium containing zeolite.

The catalyst according to (a1), comprising the titanium zeolite of framework structure type MWW, can consist of the titanium zeolite of framework structure type MWW, preferably consist of the TiMWW or the ZnTiMWW as described. In such cases, the catalyst can be the titanium zeolite of framework structure type MWW in the form of the zeolitic powder which can be molded, for example as a granules, a microsphere such as a microsphere obtained from spray drying or by a spray granulation, a shaped body having, for example, the shape of a pellet, a tablet, a cylinder, a wheel, a star or a sphere.

Preferably, the catalyst according to (a1), comprising the titanium zeolite of framework structure type MWW, preferably the TiMWW or the ZnTiMWW, is prepared as a molding comprising the titanium zeolite of framework structure type MWW, preferably the TiMWW or the ZnTiMWW, by suitably mixing the titanium zeolite of framework structure type MWW with at least one binder and/or with at least one binder precursor, and optionally at least one pore-forming agent and/or at least one plasticizing agent. The moldings may be shaped in every conceivable geometry such as strands, for example having rectangular, triangular hexagonal, quadratic, oval, or circular cross-section, stars, tablets, spheres, hollow cylinders, and the like. Examples of such binders are metal oxides, such as, for example, $SiO_2$, $Al_2O_3$, $TiO_2$, $ZrO_2$ or MgO or clays or mixtures of two or more of these oxides or mixed oxides of at least two of Si, Al, Ti, Zr, and Mg, with $SiO_2$ being preferred. Pore-forming agent such as mesopore-forming agents include polymeric vinyl compounds, such as polyalkylene oxides like polyethylene oxides, polystyrene, polyacrylates, polymethacrylates, polyolefins, polyamides and polyesters. Pasting agents include organic, in particular hydrophilic polymers, such as carbohydrates like cellulose, cellulose derivatives, such as methyl cellulose, and starch, such as potato starch, wallpaper plaster, polyacrylates, polymethacrylates, polyvinyl alcohol, polyvinyl pyrrolidone, polyisobutene or polytetrahydrofuran. The use of water, alcohols or glycols or mixtures thereof, such as mixtures of water and alcohol, or water and glycol, such as for example water and methanol, or water and ethanol, or water and propanol, or water and propylene glycol, as pasting agents may be mentioned. Preferably, the catalyst according to (a1), is employed as a molding having the shape of an extrudates, preferably an extrudates having a length of preferably from 1 to 10 mm, more preferably of from 1 to 7 mm, more preferably of from 1 to 5 mm, and a diameter preferably of from 0.1 to 5 mm, more preferably of from 0.2 to 4 mm, more preferably of from 0.5 to 2 mm. In particular as far as the preferred catalyst according to (a1) is concerned comprising the ZnTiMWW, it is preferred to employ this catalyst in the form of a micropowder or in the form of a molding, wherein the molding preferably contains said micropowder.

Said catalyst according to (a1) in the form of a micropowder, comprising the ZnTiMWW, is preferably characterized by the following features and embodiments, including the combinations of embodiments according to the given dependencies:

1. A micropowder, the particles of which having a Dv10 value of at least 2 micrometer, said micropowder comprising mesopores having an average pore diameter (4V/A) in the range of from 2 to 50 nm as determined by Hg porosimetry according to DIN 66133, and comprising, based on the weight of the micropowder, at least 95 weight-% of a microporous aluminum-free zeolitic material of structure type MWW containing titanium and zinc (ZnTiMWW). The Dv10 value is understood as being determined according to Reference Example 8 of WO 2013/117536.

2. The micropowder of embodiment 1, having a Dv10 value in the range of from 2 to 5.5 micrometer, preferably from 3 to 5.5 micrometer.

3. The micropowder of embodiment 1 or 2, having a Dv50 value in the range of from 7 to 25 micrometer and optionally a Dv90 value in the range of from 26 to 85 micrometer. The Dv50 and Dv90 values are understood as being determined according to Reference Example 8 of WO 2013/117536.
4. The micropowder of any of embodiments 1 to 3, wherein the mesopores have an average pore diameter (4V/A) in the range of from 10 to 50 nm, preferably of from 15 to 40 nm, more preferably of from 20 to 30 nm, as determined by Hg porosimetry according to DIN 66133.
5. The micropowder of any of embodiments 1 to 4, additionally comprising macropores having an average pore diameter (4V/A) in the range of from more than 50 nm, said macropores preferably having an average pore diameter in the range of from 0.05 to 3 micrometer, as determined by Hg porosimetry according to DIN 66133.
6. The micropowder of any of embodiments 1 to 5, wherein the micropores of the ZnTiMWW have an average pore diameter in the range of from 1.0 to 1.2 nanometer as determined by nitrogen adsorption according to DIN 66135.
7. The micropowder of any of embodiments 1 to 6, comprising, based on the weight of the micropowder, at least 99 weight-%, preferably at least 99.7 weight-% of the ZnTiMWW.
8. The micropowder of any of embodiments 1 to 7, wherein the ZnTiMWW contains zinc in an amount of from 1.0 to 2.0 weight-%, preferably of from 1.2 to 1.9 weight-%, calculated as Zn and based on the weight of the ZnTiMWW.
9. The micropowder of any of embodiments 1 to 8, wherein the ZnTiMWW contains titanium in an amount of from 1.0 to 2.0 weight-%, preferably of from 1.2 to 1.8 weight-%, calculated as Ti and based on the weight of the ZnTiMWW.
10. The micropowder of any of embodiments 1 to 9, having a crystallinity, as determined by X-ray diffraction (XRD) analysis, of at least (80+/−10) %, preferably of at least (85+/−10) %. The crystallinity is understood as being determined according to Reference Example 10 of WO 2013/117536.
11. The micropowder of any of embodiments 1 to 10, comprising, based on the total weight of the micropowder and calculated as element, less than 0.001 weight-%, preferably less than 0.0001 weight-% of a noble metal, preferably selected from the group consisting of gold, silver, platinum, palladium, iridium, ruthenium, osmium, and a mixture of two or more thereof, more preferably selected from the group consisting of gold, platinum, gold, and a mixture of two or more thereof.
12. The micropowder of any of embodiments 1 to 11, comprising, based on the total weight of the micropowder and calculated as element, less than 0.1 weight-%, preferably less than 0.01 weight-% of boron.
13. The micropowder of any of embodiments 1 to 12, having a bulk density of in the range of from 80 to 100 g/ml.
14. The micropowder of any of embodiments 1 to 13, being a spray powder, preferably obtainable or obtained by spray-drying.

Further, said catalyst according to (a1) in the form of a molding, comprising the ZnTiMWW, is preferably characterized by the following features and embodiments, including the combinations of embodiments according to the given dependencies:
1. A molding, comprising a microporous aluminum-free zeolitic material of structure type MWW containing titanium and zinc (ZnTiMWW), said molding preferably comprising a micropowder comprising, based on the weight of the micropowder, at least 95 weight-% of a microporous aluminum-free zeolitic material of structure type MWW containing titanium and zinc (ZnTiMWW), said molding more preferably comprising the micropowder according to any of the micropowder embodiments 1 to 14 as described hereinabove, the molding preferably further comprising at least one binder, preferably a silica binder.
2. The molding of embodiment 1, comprising mesopores having an average pore diameter in the range of from 4 to 40 nm, preferably from 20 to 30 nm as determined by Hg porosimetry according to DIN 66133.
3. The molding of embodiment 1 or 2, having a crystallinity, as determined by XRD analysis, of at least (55+/−10) %, preferably in the range of from ((55 to 75)+/−10) %. The crystallinity is understood as being determined according to Reference Example 10 of WO 2013/117536.
4. The molding of any of embodiments 1 to 3, comprising the micropowder in an amount in the range of from 70 to 80 weight-% and the silica binder in an amount of from 30 to 20 weight-%, the micropowder together with the silica binder constituting at least 99 weight-% of the molding, wherein the molding has a concentration of silanol groups with respect to the total number of Si atoms of at most 6%, preferably at most 3%, as determined according to $^{29}$Si MAS NMR. The concentration of the silanol groups is understood as being determined according to Reference Example 3 of WO 2013/117536.
5. The molding of any of embodiments 1 to 4, being a strand having circular cross-section and a diameter in the range of from 1.5 to 1.7 mm and having a crush strength of at least 5 N, preferably in the range of from 5 to 20 N, more preferably in the range of from 12 to 20 N, the crush strength being determined by crush strength test machine Z2.5/TS1S according to the method as described in Reference Example 2 of of WO 2013/117536.
6. The molding of any of embodiments 1 to 5, the $^{29}$Si-NMR spectrum of said molding comprising six peaks at the following position
peak 1 at −98+/−x ppm,
peak 2 at −104+/−x ppm,
peak 3 at −110+/−x ppm,
peak 4 at −113+/−x ppm,
peak 5 at −115+/−x ppm,
peak 6 at −118+/−x ppm,
with x in any of the peaks being 1.5, preferably 1.0, more preferably 0.5,
wherein Q which is defined as $$Q=100*\{[a_1+a_2]/[a_4+a_5+a_6]\}/a_3$$

is at most 2.5, preferably at most 1.6, preferably at most 1.4, with $[a_1+a_2]$ being the sum of the peak areas of peaks 1 and 2, and $[a_4+a_5+a_6]$ being the sum of the peak areas of peaks 4, 5, and 6, and $a_3$ being the peak area of peak 3. These $^{29}$Si-NMR characteristics are understood as being determined according the Reference Example 4 of WO 2013/117536.
7. The molding of any of embodiments 1 to 6, having a water uptake in the range of from 3 to 8 weight-%, preferably from 4 to 7 weight-%. The water uptake is understood as being determined according to Reference Example 6 of WO 2013/117536.
8. The molding of any of embodiments 1 to 7, the infrared spectrum of said molding comprising a band in the region of (3700-3750)+/−20 cm$^{-1}$ and a band in the region of (3670-3690)+/−20 cm$^{-1}$, wherein the intensity ratio of the band in the region of (3700-3750)+/−20 cm$^{-1}$ relative to the band in the region of (3670-3690)+/−20 cm$^{-1}$ is at most 1.5, preferably at most 1.4. These IR characteristics are understood as being determined according the Reference Example 5 of WO 2013/117536.

Further, a preferred process for the preparation of said catalyst according to (a1) in the form of a micropowder and/or molding, comprising the ZnTiMWW, is characterized by the following features and embodiments, including the combinations of embodiments according to the given dependencies:

1. A process comprising
    (a) providing a suspension containing a microporous aluminum-free zeolitic material of structure type MWW containing titanium and zinc (ZnTiMWW);
    (b) subjecting the suspension provided in (a) to spray-drying to obtain a micropowder;
    (c) optionally calcining the micropowder obtained in (b), wherein the micropowder obtained in (b) or (c), preferably in (c), is preferably the micropowder according to any of said micropowder embodiments 1 to 14 as described above.
2. The process of embodiment 1, wherein the suspension provided in (a) has a solid content in the range of from 5 to 25 weight-%, preferably of from 10 to 20 weight-%, the suspension preferably being an aqueous suspension.
3. The process of embodiment 1 or 2, wherein the ZnTiMWW according to (a) contains zinc in an amount of from 1.0 to 2.0 weight-%, preferably of from 1.2 to 1.9 weight-%, calculated as Zn, and titanium in an amount of from 1.0 to 2.0 weight-%, preferably of from 1.2 to 1.8 weight-%, calculated as Ti and based on the weight of the ZnTiMWW.
4. The process of any of embodiments 1 to 3, wherein in (b), a spray-apparatus, preferably a spray-tower is used for spray-drying the suspension, said apparatus having at least one spray-nozzle, preferably at least one two-component nozzle, said nozzle having a diameter in the range of from 3.5 to 4.5 mm.
5. The process of any of embodiments 1 to 4, wherein in (b), a spray-apparatus, preferably a spray-tower is used for spray-drying the suspension, said apparatus being operated with a nozzle gas having a temperature in the range of from 20 to 50° C., preferably of from 20 to 30° C., and a drying gas having a temperature in the range of from 250 to 350° C., preferably of from 275 to 325° C., said nozzle gas preferably being an inert gas, more preferably technical nitrogen, and said drying gas preferably being an inert gas, more preferably technical nitrogen.
6. The process of any of embodiments 1 to 5, wherein in (c), the micropowder is calcined at a temperature in the range of from 600 to 700° C. for a duration in the range of from 0.5 to 6 h.
7. The process of any of embodiments 1 to 6, further comprising
    (d) shaping the micropowder obtained in (b) or (c) to obtain a molding;
    (e) optionally drying and/or calcining the molding obtained in (d).
8. The process of embodiment 7, wherein the shaping according to (d) comprises
    (aa) mixing the micropowder with a binder or a binder precursor, preferably a silica binder or a silica binder precursor, wherein the weight ratio of the ZnTiMWW contained in the micropowder relative to silica contained in or resulting from the silica binder is in the range of from 3:7 to 1:4, to obtain a mixture;
    (bb) shaping the mixture obtained in (aa) to obtain a molding, said shaping preferably comprising subjecting the mixture obtained in (aa) to extrusion from which preferably strands are obtained having a diameter preferably in the range of from 1.0 to 2.0 mm, more preferably of from 1.5 to 1.7 mm.
9. The process of embodiment 8, wherein in (aa), a carbohydrate and/or water is/are added as pasting agent.
10. The process of embodiment 8 or 9, wherein the mixing in (aa) is carried out for a duration in the range of from 15 to 60 min, preferably of from 30 to 55 min, more preferably of from 40 to 50 min.
11. The process of any of embodiments 7 to 10, wherein in (d), no mesopore-forming agent selected from the group consisting of polyalkylene oxides such as polyethylene oxides, polystyrene, polyacrylates, polymethacrylates, polyolefins, polyamides, and polyesters is added.
12. The process of any of embodiments 7 to 11, wherein in (e), the molding is dried at a temperature in the range of from 100 to 150° C. for a duration in the range of from 10 to 20 h and calcined at a temperature in the range of from 500 to 600° C. for a duration in the range of from 0.5 to 2 h.
13. The process of any of embodiments 7 to 12, further comprising
    (f) subjecting the molding obtained in (d) or (e), preferably in (e), to a water-treatment;
    (g) optionally drying and/or calcining the water-treated molding, wherein the molding obtained in (f) or (g), preferably in (g), is preferably the molding according to any of said molding embodiments 1 to 8 as described above.
14. The process of embodiment 13, wherein in (f), the water-treatment comprises treating the molding with liquid water in an autoclave under autogenous pressure at a temperature in the range of from 100 to 200° C., preferably of from 125 bis 175° C., more preferably of from 140 to 150° C. for a period of from 2 to 24 hours, preferably of from 6 to 10 h.
15. The process of embodiment 13 or 14, wherein in (f), the weight ratio of the molding relative to the water is in the range of from 0.02 to 0.08, preferably of from 0.03 to 0.07, more preferably of from 0.04 to 0.06.
16. The process of any of embodiments 13 to 15, wherein in (g), the water-treated molding is dried at a temperature in the range of from 100 to 150° C. for a duration in the range of from 10 to 20 h and calcined at a temperature in the range of from 400 to 500° C. for a duration in the range of from 1 to 3 h.
17. The process of any of embodiments 7 to 16, wherein the molding is not subjected to steaming.

Regarding said preferred process for the preparation of said catalyst according to (a1) in the form of a micropowder and/or a molding, comprising the ZnTiMWW, described above by embodiments 1 to 17, the ZnTiMWW based on which the suspension in embodiment 1.(a) is provided, can be prepared according to all conceivable methods. For example, it is possible to prepare a microporous aluminum-free zeolitic material of structure type MWW containing titanium (TiMWW) and subject the TiMWW to a suitable treatment to obtain the ZnTiMWW. Further, it is possible to prepare an aluminum-free zeolitic material of structure type MWW (MWW) and subject the MWW to a suitable treatment to obtain the ZnTiMWW wherein, for example, both Zn and Ti are suitably incorporated in the MWW. Further, it is conceivable to prepare aluminum-free zeolitic material of structure type MWW wherein, during the synthesis of the MWW-type framework, Ti is introduced and the resulting material is subjected to a suitable treatment to incorporate Zn, or Zn is introduced and the resulting material is subjected to a suitable treatment to incorporate Ti, or both Zn and Ti are introduced. As conceivable methods for the preparation of TiMWW, the processes as described, for example, in U.S. Pat. No. 6,114,551, or in Wu et al., "Hydrothermal Synthesis of a novel Titanosilicate with MWW Topology", Chemistry Letters (2000), pp. 774-775 may be mentioned. Preferably, an aluminum-free zeolitic material of structure type MWW containing Ti (TiMWW) is prepared in a first stage, and in a second stage, the TiMWW is subjected to a suitable treatment to obtain the ZnTiMWW. More preferably, the ZnTiMWW is prepared according to a process comprising (I) preparing an aluminum-free zeolitic material of structure type MWW containing boron (B-MWW);
(II) deboronating the B-MWW to obtain an aluminum-free zeolitic material of structure type MWW (MWW);
(III) incorporating titanium (Ti) into the MWW to obtain an aluminum-free zeolitic material of structure type MWW containing Ti (TiMWW);
(IV) preferably acid-treating the TiMWW;
(V) subjecting the TiMWW to zinc (Zn) impregnation to obtain the ZnTiMWW.

Preferably, in stage (I), the B-MWW is prepared by a process whose preferred steps and conditions are defined by the following embodiments 1 to 28 and the respective dependencies as indicated:

1. A process for preparing an aluminum-free boron containing zeolitic material comprising the framework structure MWW (B-MWW), comprising
   (a) hydrothermally synthesizing a B-MWW precursor from a synthesis mixture containing water, a silicon source, a boron source, and an MWW template compound obtaining the B-MWW precursor in its mother liquor, the mother liquor having a pH above 9;
   (b) adjusting the pH of the mother liquor, obtained in (a) and containing the B-MWW precursor, to a value in the range of from 6 to 9;
   (c) separating the B-MWW precursor from the pH-adjusted mother liquor obtained in (b) by filtration in a filtration device.
2. The process of embodiment 1, wherein in (a), at least 95 weight-%, preferably at least 99 weight-%, more preferably at least 99.9 weight-% of the synthesis mixture consist of the water, the silicon source, the boron source, and the template compound.
3. The process of embodiment 1 or 2, wherein in (a), the silicon source is selected from the group consisting of fumed silica, colloidal silica, and a mixture thereof, the silicon source preferably being colloidal silica, more preferably ammonia-stabilized silica, the boron source is selected from the group consisting of boric acid, borates, boron oxide, and a mixture of two or more thereof, the boron source preferably being boric acid, and the MWW template compound selected from the group consisting of piperidine, hexamethylene imine, N,N,N,N',N',N'-hexamethyl-1,5-pentanediammonium ion, 1,4-bis(N-methylpyrrolidinium) butane, octyltrimethylammonium hydroxide, heptyltrimethyl-ammonium hydroxide, hexyltrimethylammonium hydroxide, N,N,N-trimethyl-1-adamantyl-ammonium hydroxide, and a mixture of two or more thereof, the MWW template compound preferably being piperidine.
4. The process of any of embodiments 1 to 3, wherein in (a), the synthesis mixture contains the boron source, calculated as elemental boron, relative to the silicon source, calculated as elemental silicon, in a molar ratio in the range of from 0.4:1 to 2.0:1, preferably from 0.6:1 to 1.9:1, more preferably from 0.9:1 to 1.4:1, the water relative to the silicon source, calculated as elemental silicon, in a molar ratio in the range of from 1:1 to 30:1, preferably from 3:1 to 25:1, more preferably from 6:1 to 20:1; and the template compound relative to the silicon source, calculated as elemental silicon, in a molar ratio in the range of from 0.4:1 to 2.0:1, preferably from 0.6:1 to 1.9:1, more preferably from 0.9:1 to 1.4:1.
5. The process of any of embodiments 1 to 4, wherein in (a), the hydrothermal synthesizing is carried out at a temperature in the range of from 160 to less than 180° C., preferably from 170 to 175° C., for a period of time in the range of from 1 to 72 h, preferably from 6 to 60 h, more preferably from 12 to 50 h.
6. The process of any of embodiments 1 to 5, wherein in (a), the hydrothermal synthesizing is carried out at least partially under stirring.
7. The process of any of embodiments 1 to 6, wherein in (a), the synthesis mixture additionally contains a seeding material, preferably a zeolitic material comprising the framework structure MWW, more preferably a boron containing zeolitic material comprising the framework structure MWW.
8. The process of embodiment 7, wherein the synthesis mixture contains the seeding material, relative to the silicon source, in a weight ratio in the range of from 0.01:1 to 1:1, preferably from 0.02:1 to 0.5:1, more preferably from 0.03:1 to 0.1:1, calculated as amount of seeding material in kg relative to silicon contained in the silicon source calculated as silicon dioxide in kg.
9. The process of any of embodiments 1 to 8, wherein the pH of the mother liquor obtained from (a) is above 10, preferably in the range of from 10.5 to 12, more preferably from 11 to 11.5.
10. The process of any of embodiments 1 to 9, wherein in (b), the pH of the mother liquor obtained in (a) is adjusted to a value in the range of from 6.5 to 8.5, preferably from 7 to 8.
11. The process of any of embodiments 1 to 10, wherein in (b), the pH is adjusted by a method comprising
    (aa) adding an acid to the mother liquor obtained from (a) containing the B-MWW precursor, wherein the adding is preferably carried out at least partially under stirring.
12. The process of embodiment 11, wherein in (aa), the adding is carried out at a temperature in the range of from 20 to 70° C., preferably from 30 to 65° C., more preferably from 40 to 60° C.
13. The process of embodiment 11 or 12, wherein in (aa), the acid is an inorganic acid, preferably an aqueous solution containing the inorganic acid.
14. The process of embodiment 13, wherein the inorganic acid is selected from the group consisting of phosphoric acid, sulphuric acid, hydrochloric acid, nitric acid, and a mixture of two or more thereof, the inorganic acid preferably being nitric acid.
15. The process of any of embodiments 11 to 14, the method additionally comprising
    (bb) stirring the mother liquor to which the acid was added according to (aa), wherein during (bb), no acid is added to the mother liquor.
16. The process of embodiment 15, wherein in (bb), the stirring is carried out at a temperature in the range of from 20 to 70° C., preferably from 25 to 65° C., more preferably from 30 to 60° C.
17. The process of any of embodiments 1 to 16, wherein in (b), the size of the particles contained in the mother liquor, expressed by the respective Dv10, Dv50, and Dv90 value, is increased for at least 2%, preferably at least 3%, more preferably at least 4.5% regarding Dv10, for at least 2%, preferably at least 3%, more preferably at least 4.5% regarding Dv50, and for at least 5%, preferably at least 6%, more preferably at least 7% regarding Dv90.

18. The process of any of embodiments 1 to 17, wherein the pH-adjusted mother liquor obtained from (b) has a solids content in the range of from 1 to 10 weight-%, preferably from 4 to 9 weight-%, more preferably from 7 to 8 weight-%, based on the total weight of the pH-adjusted mother liquor obtained from (b).

19. The process of any of embodiments 1 to 18, wherein the pH-adjusted mother liquor obtained from (b) has a filtration resistance in the range of from 10 to 50 mPa*s/m$^2$, preferably from 15 to 45 mPa*s/m$^2$, more preferably from 20 to 40 mPa*s/m$^2$.

20. The process of any of embodiments 1 to 19, further comprising
    (d) washing the B-MWW precursor obtained from (c), preferably the filter cake obtained from (c), wherein the washing is preferably performed using water was washing agent.

21. The process of embodiment 20, wherein in (d), the filter cake obtained from (c) is has a washing resistance in the range of from 10 to 50 mPa*s/m$^2$, preferably from 15 to 45 mPa*s/m$^2$, more preferably from 20 to 40 mPa*s/m$^2$.

22. The process of embodiment 20 or 21, wherein the washing is carried out until the conductivity of the filtrate is at most 300 microSiemens/cm, preferably at most 250 microSiemens/cm, more preferably at most 200 microSiemens/cm.

23. The process of any of embodiments 1 to 22, further comprising
    (e) drying the B-MWW precursor obtained from (c), preferably from (d), at a temperature in the range of from 20 to 50° C., preferably from 20 to 40° C., more preferably from 20 to 30° C., wherein the drying is preferably carried out by subjecting the B-MWW to a gas stream, preferably a nitrogen stream.

24. The process of any of embodiments 1 to 23, wherein the residual moisture of the B-MWW precursor obtained from (c), preferably from (d), more preferably from (e), is in the range of from 80 to 90 weight-%, preferably from 80 to 85 weight-%.

25. The process of any of embodiments 1 to 24, further comprising
    (f) preparing a suspension, preferably an aqueous suspension, containing the B-MWW precursor obtained from to (c), preferably from (d), more preferably from (e), and having a solids content in the range of from 10 to 20 weight-%, preferably from 12 to 18 weight-%, more preferably from 14 to 16 weight-%;
    (g) spray drying the suspension obtained from (f) containing the B-MWW precursor, obtaining a spray powder;
    (h) calcining the spray powder obtained from (g) containing the B-MWW precursor, preferably at a temperature in the range of from 500 to 700° C., more preferably from 550 to 650° C., more preferably from 575 to 625° C. for a period of time in the range of from 1 to 24 h, preferably from 2 to 18 h, more preferably from 6 to 12 h, obtaining a spray powder of which at least 99 weight-%, more preferably at least 99.5 weight-% consist of the B-MWW.

26. The process of embodiment 25, wherein in (h), the calcining is carried out in continuous mode, preferably in a rotary calciner, preferably at a throughput in the range of from 0.5 to 20 kg spray powder per h.

27. The process of embodiment 25 or 26, wherein the degree of crystallinity of the B-MWW contained in the spray powder obtained from (h) is at least (75±5) %, preferably at least (80±5) %, as determined via XRD.

28. The process of any of embodiments 25 to 27, wherein the BET specific surface area of the B-MWW contained in the spray powder obtained from (h) is at least 300 m$^2$/g, preferably in the range of from 300 to 500 m$^2$/g, as determined according to DIN 66131.

Preferably, stage (II) is carried by a process whose preferred steps and conditions are defined by the following embodiments 1 to 7 and the respective dependencies as indicated:

1. A process for the preparation of a zeolitic material, comprising
    (a) providing the boron-containing zeolitic material of structure type MWW (B-MWW) obtained according to stage (I);
    (b) deboronating the B-MWW by treating the B-MWW with a liquid solvent system thereby obtaining a deboronated B-MWW (MWW);
    wherein the liquid solvent system is selected from the group consisting of water, monohydric alcohols, polyhydric alcohols, and mixtures of two or more thereof, and wherein said liquid solvent system does not contain an inorganic or organic acid or a salt thereof, the acid being selected from the group consisting of hydrochloric acid, sulfuric acid, nitric acid, phosphoric acid, formic acid, acetic acid, propionic acid, oxalic acid, and tartaric acid.

2. The process of embodiment 1, wherein the liquid solvent system does not contain an inorganic or organic acid, or a salt thereof.

3. The process of embodiment 1 or 2, wherein the liquid solvent system is selected from the group consisting of water, methanol, ethanol, propanol, ethane-1,2-diol, propane-1,2-diol, propane-1,3-diol, propane-1,2,3-triol, and mixtures of two or more thereof, preferably water.

4. The process of any of embodiments 1 to 3, wherein the treating according to (b) is carried out at a temperature in the range of from 50 to 125° C.

5. The process of any of embodiments 1 to 4, wherein the treating according to (b) is carried out for a time in the range of from 6 to 20 h.

6. The process of any of embodiments 1 to 5, wherein the treating according to (b) is carried out in at least 2 separate steps, wherein between at least 2 treating steps, the MWW is dried, preferably at a temperature in the range of from 100 to 150° C.

7. The process of any of embodiments 1 to 6, further comprising
    (c) post-treating the MWW obtained from (b) by a process comprising
    (c.1) separating the MWW from the liquid solvent system;
    (c.2) preferably drying the separated MWW, preferably by spray-drying;
    (c.3) optionally calcining the MWW obtained from (c.1) or (c.2), preferably at temperatures in the range of from 500 to 700° C.

As far as stage (III) is concerned, preferably a suitable starting mixture, preferably an aqueous mixture, containing the MWW and a Ti containing precursor, and preferably containing at least one suitable micropore-forming agent, is subjected to hydrothermal crystallization under autogenous pressure. It may be conceivable to use at least one suitable seeding material. As suitable Ti containing precursor, tetraalkylorthotitanates such as tetrabutyl orthotitanate may be mentioned by way of example. As suitable micropore-forming agent, piperidine, hexamethylene imine, or mixtures of piperidine and hexamethylene imine may be mentioned by way of example. Preferably, the crystallization time is in the range of from 4 to 8 days, more preferably from 4 to 6 days. During hydrothermal synthesis, the crystallization mixture may be stirred. The temperatures applied during crystallization are preferably in the range of from 160 to 200° C., more preferably from 160 to 180° C. After hydrothermal synthesis, the obtained crystalline zeolitic material TiMWW is preferably suitably separated from the mother liquor. All methods of separating the TiMWW from its mother liquor are conceivable. These methods include, for example, filtration, ultrafiltration, diafiltration and centrifugation methods or, for instance, spray drying processes and spray granulation processes. A combination of two or more of these methods can be applied. According to the present invention, the TiMWW is preferably separated from its mother liquid by filtration to obtain a filter cake which is preferably subjected to washing, preferably with water. Subsequently, the filter cake, optionally further processed to obtained a suitable suspension, is subjected to spray drying or to ultrafiltration. Prior to separating the TiMWW from its mother liquor, it is possible to increase the TiMWW content of the mother liquor by concentrating the suspension. If washing is applied, it is preferred to continue the washing process until the washing water has a conductivity of less than 1,000 microSiemens/cm, more preferably of less than 900 microSiemens/cm, more preferably of less than 800 microSiemens/cm, more preferably of less than 700 microSiemens/cm. After separation of the TiMWW from its mother liquor, preferably achieved via filtration, and after washing, the washed filter cake containing the TiMWW is preferably subjected to pre-drying, for example by subjecting the filter cake to a suitable gas stream, preferably a nitrogen stream, for a time preferably in the range of from 4 to 10 h, more preferably from 5 to 8 h. Subsequently, the pre-dried filter cake is preferably dried at temperatures in the range of from 100 to 300° C., more preferably from 150 to 275° C., more preferably from 200 to 250° C. in a suitable atmosphere such as technical nitrogen, air, or lean air, preferably in air or lean air. Such drying can be accomplished, for example, by spray-drying. After drying, the TiMWW may be subjected to calcination at temperatures in the range of from 500 to 700° C., more preferably from 550 to 675° C., more preferably from 600 to 675° C. in a suitable atmosphere such as technical nitrogen, air, or lean air, preferably in air or lean air. Preferably, no calcination is carried out according to (III).

Preferably, stages (III) and (IV) are carried out by a process whose preferred steps and conditions are defined by the following embodiments 1 to 27 and the respective dependencies as indicated:

1. A process for the preparation of a titanium-containing zeolitic material having an MWW framework structure comprising
   (a) providing the deboronated crystalline zeolitic material MWW obtained according to stage (II);
   (b) incorporating titanium into the zeolitic material provided in (a) comprising
      (b.1) preparing an aqueous synthesis mixture containing the zeolitic material provided in (i), an MWW template compound and a titanium source, wherein the molar ratio of the MWW template compound relative to Si, calculated as $SiO_2$ and contained in the zeolitic material provided in (a), is in the range of from 0.5:1 to 14:1;
      (b.2) hydrothermally synthesizing a titanium-containing zeolitic material having an MWW framework structure from the aqueous synthesis mixture prepared in (b.1), obtaining a mother liquor comprising the titanium-containing zeolitic material having an MWW framework structure;
   (c) spray-drying the mother liquor obtained from (b.2) comprising the titanium-containing zeolitic material having an MWW framework structure.
2. The process of embodiment 1, wherein in (b.1), the MWW template compound is selected from the group consisting of piperidine, hexamethylene imine, N,N,N,N',N',N'-hexamethyl-1,5-pentanediammonium ion, 1,4-bis (N-methylpyrrolidini-um)butane, octyltrimethylammonium hydroxide, heptyltrimethylammonium hydroxide, hexyltrimethylammonium hydroxide, and a mixture of two or more thereof, the MWW template compound preferably being piperidine.
3. The process of embodiment 1 or 2, wherein in (b.1), the titanium source is selected from the group consisting of tetrabutyl orthotitanate, tetraisopropyl orthotitanate, tetraethyl orthotitanate, titanium dioxide, titanium tetrachloride, titanium tert-butoxide, and a mixture of two or more thereof, the titanium source preferably being tetrabutyl orthotitanate.
4. The process of any of embodiments 1 to 3, wherein in the aqueous synthesis mixture in (b.1), the molar ratio of Ti, calculated as $TiO_2$ and contained in the titanium source, relative to Si, calculated as $SiO_2$ and contained in the zeolitic material having a molar ratio $B_2O_3:SiO_2$ of at most 0.02:1, is in the range of from 0.005:1 to 0.1:1, preferably from 0.01:1 to 0.08:1, more preferably from 0.02:1 to 0.06:1.
5. The process of any of embodiments 1 to 4, wherein in the aqueous synthesis mixture in (b.1), the molar ratio of $H_2O$ relative to Si, calculated as $SiO_2$ and contained in the zeolitic material having a molar ratio $B_2O_3:SiO_2$ of at most 0.02:1, is in the range of from 8:1 to 20:1, preferably from 10:1 to 18:1, more preferably from 12:1 to 16:1.
6. The process of any of embodiments 1 to 5, wherein in the aqueous synthesis mixture in (b.1), the molar ratio of the MWW template compound relative to Si, calculated as $SiO_2$ and contained in the zeolitic material provided in (i), is in the range of from 0.5:1 to 1.7:1, preferably from 0.8:1 to 1.5:1, more preferably from 1.0:1 to 1.3:1.
7. The process of any of embodiments 1 to 6, wherein in (b.2), the hydrothermal synthesizing is carried out at a temperature in the range of from 80 to 250° C., preferably from 120 to 200° C., more preferably from 160 to 180° C.
8. The process of any of embodiments 1 to 7, wherein in (b.2), the hydrothermal synthesizing is carried out for a period in the range of from 10 to 100 h, more preferably from 20 to 80 h, more preferably from 40 to 60 h.
9. The process of any of embodiments 1 to 8, wherein in (b.2), the hydrothermal synthesizing is carried out in a closed system under autogenous pressure.
10. The process of any of embodiments 1 to 9, wherein neither during (b.2), nor after (b.2) and before (c), the titanium-containing zeolitic material having an MWW framework structure is separated from its mother liquor.
11. The process of any of embodiments 1 to 10, wherein the mother liquor subjected to (c) comprising the titanium-containing zeolitic material having an MWW framework structure has a solids content, optionally after concentration or dilution, in the range of from 5 to 25 weight-%, more preferably from 10 to 20 weight-%, based on the total weight of the mother liquor comprising the titanium-containing zeolitic material.

12. The process of any of embodiments 1 to 11, wherein during spray-drying in (c), the drying gas inlet temperature is in the range of from 200 to 350° C. and the drying gas outlet temperature is in the range of from 70 to 190° C.

13. The process of any of embodiments 1 to 12, wherein the zeolitic material having an MWW framework structure obtained from (c) has a Si content in the range of from 30 to 40 weight-%, calculated as elemental Si, a total organic carbon content (TOC) in the range of from 0 to 14 weight-%, and a Ti content of from 2.1 to 2.8 weight-%, calculated as elemental titanium, in each case based on the total weight of the zeolitic material.

14. The process of any of embodiments 1 to 13, further comprising
    (d) treating the titanium-containing zeolitic material having an MWW framework structure obtained from (iii) with an aqueous solution having a pH of at most 5.

15. The process of embodiment 14, wherein after (c) and before (d), the spray-dried titanium-containing zeolitic material having an MWW framework structure obtained from (c) is not subjected to calcination.

16. The process of embodiment 14 or 15, wherein in (d), the weight ratio of the aqueous solution relative to the titanium-containing zeolitic material having an MWW framework structure is in the range of from 10:1 to 30:1, preferably from 15:1 to 25:1, more preferably from 18:1 to 22:1.

17. The process of any of embodiments 14 to 16, wherein in (d), the aqueous solution comprises an inorganic acid, preferably selected from the group consisting of phosphoric acid, sulphuric acid, hydrochloric acid, nitric acid, and a mixture of two or more thereof, the aqueous solution preferably comprising nitric acid.

18. The process of any of embodiments 14 to 17, wherein in (d), the aqueous solution has a pH in the range of from 0 to 5, preferably from 0 to 3, more preferably from 0 to 2.

19. The process of any of embodiments 14 to 18, wherein in (d), the titanium-containing zeolitic material having an MWW framework structure is treated with the aqueous solution at a temperature in the range of from 50 to 175° C., preferably from 70 to 125° C., more preferably from 95 to 105° C.

20. The process of any of embodiments 14 to 19, wherein in (d), the titanium-containing zeolitic material having an MWW framework structure is treated with the aqueous solution for a period in the range of from 0.1 to 6 h, preferably from 0.3 to 2 h, more preferably from 0.5 to 1.5 h.

21. The process of any of embodiments 14 to 20, wherein the treating according to (d) is carried out in a closed system under autogenous pressure.

22. The process of any of embodiments 14 to 21, further comprising
    (e) separating the titanium-containing zeolitic material having an MWW framework structure obtained from (d) from the aqueous solution, optionally followed by washing the separated titanium-containing zeolitic material having an MWW framework.

23. The process of embodiment 22, wherein (e) comprises drying the separated and optionally washed titanium-containing zeolitic material having an MWW framework structure.

24. The process of any of embodiments 14 to 23, further comprising
    (f) preparing a suspension, preferably an aqueous suspension containing the titanium-containing zeolitic material having an MWW framework structure obtained from (d), preferably from (e), said suspension having a solids content preferably in the range of from 5 to 25 weight-%, more preferably from 10 to 20 weight-%, based on the total weight of the suspension, and subjecting the suspension to spray-drying.

25. The process of embodiment 24, wherein during spray-drying, the drying gas inlet temperature is in the range of from 200 to 330° C. and the drying gas outlet temperature is in the range of from 120 to 180° C.

26. The process of any of embodiments 14 to 25, further comprising
    (g) calcining the titanium containing zeolitic material having an MWW framework structure obtained from (d), preferably from (e), more preferably from (f), wherein the calcining is preferably carried out at a temperature in the range of from 400 to 800° C., more preferably from 600 to 700° C.

27. The process of embodiment 26, wherein in (vii), the calcining is carried out in continuous mode, preferably with a rate in the range of from 0.2 to 2.0 kg zeolitic material per hour, more preferably from 0.5 to 1.5 kg zeolitic material per hour.

According to stage (V), the TiMWW preferably obtained according to stage (IV) is subjected to a suitable Zn treatment to obtain the ZnTiMWW used for the preparation of the suspension according to (a). Generally, as far as (V) is concerned, no specific restrictions exist provided that above-defined preferred ZnTiMWW can be obtained having the preferred Zn and Ti content. Most preferably, stage (V) comprises at least one suitable impregnation stage, more preferably at least one wet impregnation stage. Concerning this impregnation stage, it is preferred to contact the TiMWW preferably as obtained according to (IV) is contacted with at least one suitable Zn-containing precursor in at least one suitable solvent (wet impregnation), most preferably water. As suitable Zn-containing precursor, water-soluble Zn salts are especially preferred, with zinc acetate dihydrate being especially preferred. It is further preferred to prepare a solution of the Zn-containing precursor, preferably an aqueous solution, and to suspend the TiMWW in this solution. Further preferably, impregnation is carried out at elevated temperatures, relative to room temperature, preferably in the range of from 75 to 125° C., more preferably from 85 to 115° C., for a time preferably in the range of from 3.5 to 5 h, more preferably from 3 to 6 h. Stirring the suspension during impregnation is preferred. After the impregnation, the obtained ZnTiMWW is preferably suitably separated from the suspension. All methods of separating the ZnTiMWW from the suspension are conceivable. Especially preferably, separation is carried out via filtration, ultrafiltration, diafiltration or centrifugation methods. A combination of two or more of these methods can be applied. According to the present invention, the ZnTiMWW is preferably separated from the suspension by filtration to obtain a filter cake which is preferably subjected to washing, preferably with water. If washing is applied, it may be preferred to continue the washing process until the washing water has a conductivity of less than 1,000 microSiemens/cm, more preferably of less than 900 microSiemens/cm, more preferably of less than 800 microSiemens/cm, more preferably of less than 700 microSiemens/cm. Subsequently, the preferably washed filter cake is subjected to pre-drying, for example by subjecting the filter cake to a suitable gas stream, preferably a nitrogen stream, for a time preferably in the range of from 5 to 15 h, more preferably from 8 to 12.

If TiMWW or ZnTiMWW is used as catalytically active material according to the present invention, it is preferred that the organic solvent is acetonitrile.

Generally, preferred ZnTiMWW catalyst can be prepared according to the specific teaching as disclosed in WO 2013/117536 A2 which is enclosed herein in its entirety by reference.

TS-1 Catalyst

According to the present invention, a titanium silicalite-1 catalyst, preferably a fixed-bed titanium silicalite-1 catalyst, can be employed as catalyst. Titanium silicalite-1 is a microporous zeolite of structure type MFI which contains no aluminum and in which the Si(IV) in the silicate lattice is partly replaced by titanium as Ti(IV). The term "micropores" as used in the context of the present invention relates to pores having a pore size smaller than 2 nm, determined according to DIN 66134.

The titanium silicalite-1 zeolite of the catalyst can in principle be prepared by any conceivable method. Typically, the synthesis of the at least one titanium zeolite according to the present invention is carried out in hydrothermal systems involving the combination of an active source of silicon oxide and a titanium source, such as titanium oxide, with at least one template compound capable of forming the desired titanium zeolite in an aqueous suspension, for example in a basic suspension. Typically, organic templates are employed. Preferably, the synthesis is carried out at elevated temperatures, for example temperatures in the range of from to 150 to 200° C., preferably from 160 to 180° C.

In principle, any suitable compound can be used as silicon oxide source. Typical sources of silicon oxide ($SiO_2$) include silicates, silica hydrogel, silicic acid, colloidal silica, fumed silica, tetraalkoxysilanes, silicon hydroxides, precipitated silica and clays. Both so-called "wet-process" silicon dioxide and so-called "dry-process" silicon dioxide can be employed. In these cases, the silicon dioxide is particularly preferably amorphous, wherein the size of the silicon dioxide particles is, for example, in the range of from 5 to 100 nm and the surface area of the silicon dioxide particles is, for example, in the range of from 50 to 500 $m^2$/g. Colloidal silicon dioxide is, inter alia, commercially available as Ludox®, Syton®, Nalco®, or Snowtex®. "Wet process" silicon dioxide is, inter alia, commercially available as Hi-Sil®, Ultrasil®, Vulcasil®, Santocel®, Valron-Estersil®, Tokusil® or Nipsil®. "Dry process" silicon dioxide is commercially available, inter alia, as Aerosil®, Reolosil®, Cab-O-Sil®, Fransil® or ArcSilica®. It is as well within the scope of the present invention to use a silicon dioxide precursor compound as silicon oxide source. For example, tetraalkoxysilanes, such as for example, tetraethoxysilane or tetrapropoxysilane, may be mentioned as precursor compound.

As template, any template suitable to provide the desired MFI zeolitic structure can be used. In particular, tetrapropylammonium hydroxide, more preferably tetra-n-propylammonium hydroxide is employed. In a preferred embodiment of the process according to the invention, the at least one pore forming agent is removed in a later step by calcination, as described below.

Typically, the synthesis of the titanium silicalite-1 is carried out batchwise in an autoclave so that the reaction suspension is subjected to autogenous pressure for a number of hours or a few days until the titanium silicalite-1 zeolite is obtained. According to a preferred embodiment of the present invention, the synthesis generally proceeds at elevated temperatures wherein the temperatures during the hydrothermal crystallization step are typically in the range of from 150 to 200° C., preferably in the range of from 160 to 180° C. Usually, the reaction is carried out for a time in the range of a few hours to several days, preferably for a time in the range of from 12 h to 48 h, more preferably from 20 to 30 h. It is further conceivable to add seed crystals to the synthesis batches.

According to an embodiment of the present invention, the crystalline titanium silicalite-1 obtained is separated off from the reaction suspension, i.e. from the mother liquor, optionally washed and dried.

All methods known for the separation of the crystalline titanium silicalite-1 from the suspension can be employed. Inter alia, filtration, ultra-filtration, diafiltration and centrifugation methods should be mentioned.

In case the crystalline titanium silicalite-1 obtained is washed, said washing step can be carried out employing any suitable wash substance, such as, for example, water, alcohols, such as for example, methanol, ethanol, or methanol and propanol, or ethanol and propanol, or methanol and ethanol and propanol, or mixtures of water and at least one alcohol, such as, for example, water and ethanol or water and methanol, or water and ethanol, or eater and propanol, or water and methanol and ethanol, or water and methanol and propanol, or water and ethanol and propanol or water and ethanol and methanol and propanol. Water or a mixture of water and at least one alcohol, preferably water and ethanol, are used as wash substance.

Drying of the crystalline titanium silicalite-1 is effected at temperatures, in general, in the range of from 80 to 160° C., preferably from 90 to 145° C., particularly preferably from 100 to 130° C.

Instead of the above mentioned separation methods, such as, inter alia, filtration, ultra-filtration, diafiltration and centrifugation methods, the suspension may, according to an alternative embodiment, also be subjected to spray methods, as for example spray-granulation and spray-drying.

If the separation of the crystalline titanium silicalite-1 is carried out by means of spray method, the separating and drying step can be combined to a single step. In such case, either the reaction suspension as such or a concentrated reaction suspension can be employed. Additionally, it is possible to add a suitable additive as for example at least one suitable binder and/or at least one pore forming agent to the suspension—either to the reaction suspension as such or to the concentrated suspension—prior to spray drying or spray granulation. Suitable binders are described in detail below. As pore forming agent all pore forming agents described above can be used. In case the suspension is spray-dried, the pore forming agent—if added—may be added in two manners. First, the pore forming agent can be added to the reaction mixture prior to spray drying. However, it is also possible to add a portion of the pore forming agent to the reaction mixture prior to spray drying, with the remainder of the pore forming agent being added to the spray dried material.

In case the suspension is first concentrated to enhance the content of the titanium silicalite-1 in the suspension, concentration can be achieved, for example, by evaporating, as for example evaporating under reduced pressure, or by cross flow filtration. Likewise, the suspension can be concentrated by separating said suspension into two fractions, wherein the solid contained in one of both fractions is separated off by filtration, diafiltration, ultrafiltration or centrifugation methods and is suspended after an optional washing step and/or drying step in the other fraction of the suspension. The thus obtained concentrated suspension can then be subjected to spray methods, as for example spray granulation and spray drying.

According to an alternative embodiment, concentration is achieved by separating the at least one titanium zeolite from the suspension, and re-suspending the titanium zeolite, optionally together with at least one suitable additive as already described above, wherein the titanium zeolite may be subjected to at least one washing step and/or at least one drying step prior to re-suspension. The re-suspended titanium zeolite can then be employed to spraying methods, preferably to spray drying.

Spray-drying is a direct method of drying slurries, suspensions or solutions by feeding a well-dispersed liquid-solid slurry, suspension or solution, often additionally containing a binder, to an atomizer and subsequently flash-drying in a stream of hot air. The atomizer can be of several different types. Most common is wheel atomization which uses high-speed rotation of a wheel or a disc to break up the slurry into droplets that spin out from the wheel into a chamber and are flash-dried prior to hitting the chamber walls. The atomization may also be accomplished by single fluid nozzles which rely on hydrostatic pressure to force the slurry through a small nozzle. Multi-fluid nozzles are also used, where gas pressure is used to force the slurry through the nozzle. The sprayed material obtained using spray drying and spray granulation methods, like for example fluidized-bed drying, can contain solid and/or hollow spheres and can substantially consist of such spheres, which have, for example, a diameter in the range of from 5 to 500 μm or 5 to 300 μm. Single component or multiple component nozzles can be used. The use of a rotating sprayer is also conceivable. Possible inlet temperatures for the used carrier gas are, for example, in the range of from 200 to 600° C., preferably in the range of from 300 to 500° C. The outlet temperature of the carrier gas is, for example, in the range of from 50 to 200° C. Air, lean air or oxygen-nitrogen mixtures with an oxygen content of up to 10 volume-%, preferably of up to 5 volume-%, more preferably of less than 5 volume-%, as, for example, of up to 2 volume-%, may be mentioned as carrier gases. The spray methods can be carried out in counter-current or co-current flow.

Preferably, the titanium silicalite-1 is separated from the reaction suspension by conventional filtration or centrifugation, optionally dried and/or calcined, and re-suspended, preferably in a mixture, preferably an aqueous mixture of at least one binder material and/or one pore-forming agent. The resulting suspension is then preferably subjected to spray-drying or spray-granulation. The obtained sprayed material may be subjected to an additional washing step, said washing step being carried out as described above. The optionally washed sprayed material is then dried and calcined wherein drying and calcination is preferably carried out as described above.

According to an alternative embodiment, the crystallization of the titanium silicalite-1 is effected not before the above described suspension has been spray dried. Therefore, first a suspension is formed comprising the source of silicon oxide, preferably silicon dioxide, the source of titanium oxide, and the template compound capable of forming the titanium silicalite-1. Then, the suspension is spray-dried, wherein subsequently, optionally additional pore forming agent is added to the spray-dried titanium silicalite-1.

The spray-dried titanium silicalite-1 obtained according to the above mentioned processes can, optionally, be subjected to at least one wash process. If at least one wash process is carried out, preferably at least one drying step and/or at least one calcination step follows.

The titanium silicalite-1, optionally obtained by spraying methods, can further be subjected to at least one calcination step, which is carried out according to a preferred embodiment of the invention subsequent to the drying step, or instead of the drying step. The at least one calcination step is carried out at temperatures in general in the range of from 350 to 750° C., preferably form 400 to 700° C., particularly preferably from 450 to 650° C.

The calcination of the titanium silicalite-1 can be effected under any suitable gas atmosphere, wherein air and/or lean air is preferred. Furthermore, the calcinations is preferably carried out in a muffle furnace, rotary cone and/or a belt calcination furnace, wherein the calcination is generally carried out for one hour or more, for example for a time in the range of from 1 to 24 or from 4 to 12 hours. It is possible in the process according to the present invention, for example, to calcine the titanium silicalite-1 once, twice or more often for in each case at least one hour, for example in each case from 4 to 12 h, preferably from 4 to 8 h, wherein it is possible to keep the temperatures during the calcination step constant or to change the temperatures continuously or discontinuously. If calcination is effected twice or more often, the calcination temperatures in the individual steps may be different or identical.

Thus, a preferred embodiment of the present invention relates to a process as described above, wherein the titanium silicalite-1 separated off from the suspension, for example by filtration or spray drying, is washed with a suitable wash substance, and subsequently subjected to at least one drying step. Drying is effected at temperatures, in general, in the range of from 80 to 160° C., preferably from 90 to 145° C., particularly preferably from 100 to 130° C. Most preferably, after drying, a calcinations step is performed. The step is carried out at temperatures in general in the range of from 350 to 750° C., preferably form 400 to 700° C., particularly preferably from 450 to 650° C.

The titanium silicalite-1, prepared as described above, generally can be directly employed as catalyst in stages (i) and (iii). However, it is especially preferred to use a fixed-bed catalyst in both stages (i) and (iii), i.e. to employ not the crystalline zeolitic material per se as catalyst but the crystalline material processed to give a molding comprising the titanium silicalite-1. Thus, according to a preferred embodiment, a molding comprising the titanium silicalite-1, as described above, is employed as catalyst.

In general, in case a molding is employed as catalyst, said catalyst may comprise all conceivable further compounds in addition to the titanium silicalite-1 according to the invention, for example, inter alia, at least one binder and/or at least one pore forming agent. Furthermore, the catalyst may comprise at least one pasting agent instead of the at least one binder and/or the at least one pore forming agent or in addition to the at least one binder and/or the at least one pore forming agent.

As binder all compounds are suitable, which provide adhesion and/or cohesion between the titanium silicalite-1 to be shaped which goes beyond the physisorption which may be present without a binder. Examples of such binders are metal oxides, such as, for example, $SiO_2$, $Al_2O_3$, $TiO_2$, $ZrO_2$ or MgO or clays or mixtures of two or more of these compounds. Clay minerals and naturally occurring or synthetically produced aluminas, such as, for example, alpha-, beta-, gamma-, delta-, eta-, kappa-, chi- or theta-alumina and their inorganic or organometallic precursor compounds, such as, for example, gibbsite, bayerite, boehmite or pseudoboehmite or trialkoxyaluminates, such as, for example, aluminum triisopropylate, are particularly preferred as $Al_2O_3$ binders. Further preferred binders are amphiphilic compounds having a polar and a nonpolar moiety and graphite. Further binders are, for example, clays, such as, for example, montmorillonites, kaolins, metakaoline, hectorite, bentonites, halloysites, dickites, nacrites or anaxites.

These binders can be used as such. It is also within the scope of the present invention to use compounds from which the binder is formed in at least one further step in the production of the moldings. Examples of such binder precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate.

In the context of the present invention binders which either completely or partly comprise $SiO_2$, or which are a precursor of $SiO_2$, from which $SiO_2$ is formed in at least one further step, are very particularly preferred. In this context, both colloidal silica and so-called "wet process" silica and so-called "dry process" silica can be used. Particularly preferably this silica is amorphous silica, the size of the silica particles being, for example, in the range of from 5 to 100 nm and the surface area of the silica particles being in the range of from 50 to 500 $m^2/g$.

Colloidal silica, preferably as an alkaline and/or ammoniacal solution, more preferably as an ammoniacal solution, is commercially available, inter alia, for example as Ludox®, Syton®, Nalco® or Snowtex®. "Wet process" silica is commercially available, inter alia, for example as Hi-Sil®, Ultrasil®, Vulcasil®, Santocel®, Valron-Estersil®, Tokusil® or Nipsil®. "Dry process" silica is commercially available, inter alia, for example as Aerosil®, Reolosil®, Cab-O-Sil®, Fransil® or ArcSilica®. Inter alia, an ammoniacal solution of colloidal silica is preferred in the present invention. Accordingly, the present invention also describes a catalyst containing a molding, as described above, said molding comprising the titanium silicalite-1 as described above and additionally $SiO_2$ as binder material wherein the binder used according to (I) is a binder comprising or forming $SiO_2$. Generally, the titanium zeolite can also be shaped without using a binder.

Thus, the present invention also relates to a process, wherein in stages (i) and (iii), the titanium silicalite-1 catalyst is obtained by shaping the titanium silicalite-1 to give a molding comprising the titanium silicalite-1 and preferably at least one binder, in particular a silica binder.

If desired, at least on pore forming agent can be added to the mixture of titanium silicalite-1 and at least one binder or at least binder-precursor, for further processing and for the formation of the catalyst shaped body to be employed as fixed-bed catalyst. Pore forming agents which may be used are all compounds which, with regard to the molding produced, provide a specific pore size and/or a specific pore size distribution and/or certain pore volumes. In particular, pore forming agents which provide, with regard to the molding produced, micropores and/or micropores, in particular mesopores and micropores.

Thus, the present invention also relates to a process, wherein in stages (i) and (iii), the titanium silicalite-1 catalyst is obtained by shaping the titanium silicalite-1 to give a molding comprising the titanium silicalite-1 and preferably at least one binder, in particular a silica binder, the molding in particular having micropores and mesopores.

As regards examples for pore forming agents which may be used, reference is made to the pore forming agents already mentioned above. Preferably, the pore forming agents used in the shaping process of the invention are polymers which are dispersible, suspendable or emulsifiable in water or in aqueous solvent mixtures. Especially preferred polymers are polymeric vinyl compounds, such as, for example, polyalkylene oxides, such as polyethylene oxides, polystyrene, polyacrylates, polymethacrylates, polyolefins, polyamides and polyesters, carbohydrates, such as, for example, cellulose or cellulose derivatives, such as, for example, methyl cellulose, or sugars or natural fibers. Further suitable pore forming agents are, for example, pulp or graphite.

If desired for the pore size distribution to be achieved, a mixture of two or more pore forming agents may be used. In a particularly preferred embodiment of the process according to the invention, as described below, the pore forming agents are removed by calcination to give the porous catalyst shaped body. Preferably, pore forming agents which provide mesopores and/or micropores, particularly preferably mesopores, are added to the mixture of at least one binder and titanium silicalite-1 for shaping the titanium silicalite-1. Generally, the titanium silicalite-1 can also be shaped to obtain a catalyst shaped body without using a pore forming agent.

Besides binder and optionally pore forming agent it is as well possible to add additional components, for example at least one pasting agent, to the mixture which is shaped to obtain the catalyst shaped body.

If at least one pasting agent is used, said pasting agent is used either instead of or in addition to the at least one pore forming agent. In particular, compounds which also act as pore forming agents can be used as pasting agent. Pasting agents which may be used are all compounds known to be suitable for this purpose. These are preferably organic, in particular hydrophilic polymers, such as, for example, cellulose, cellulose derivatives, such as, for example, methyl cellulose, and starch, such as, for example, potato starch, wallpaper plaster, polyacrylates, polymethacrylates, polyvinyl alcohol, polyvinylpyrrolidone, polyisobutene or polytetrahydrofuran. The use of water, alcohols or glycols or mixtures thereof, such as mixtures of water and alcohol, or water and glycol, such as for example water and methanol, or water and ethanol, or water and propanol, or water and propylenglycol, as pasting agents may be mentioned. Preferably, cellulose, cellulose derivatives, water and mixtures of two or more of these compounds, such as water and cellulose or water and cellulose derivatives are used as pasting agent. In a particularly preferred embodiment of the process according to the invention, the at least one pasting agents is removed by calcination, as further described below, to give the molding.

According to a further embodiment of the present invention, at least one acidic additive can be added to the mixture which is shaped to obtain the molding. If an acidic additive is used, organic acidic compounds which can be removed by calcination, are preferred. In this context carboxylic acids, such as, for example, formic acid, oxalic acid and/or citric acid, may be mentioned. It is also possible to use two or more of these acidic compounds.

The order of addition of the components to the mixture which is shaped to obtain the molding is not critical. If for example, a combination of a binder, a pore forming agent, a pasting agent and optionally at least one acidic compound is employed, it is possible both first to add the at least one binder then the at least one pore forming agent, the at least one acidic compound and finally the at least one pasting agent and to interchange the sequence with regard to the at least one binder, the at least one pore forming agent, the at least one acidic compound and the at least one pasting agent.

After the addition of at least one binder and/or at least one pasting agent and/or at least one pore forming agent and/or at least one acidic additive to the mixture comprising the titanium silicalite-1, the mixture is typically homogenized for 10 to 180 minutes. Inter alia, kneaders, edge mills or extruders are particularly preferably used for the homogenization. The mixture is preferably kneaded. On an industrial scale, grinding in an edge mill is preferred for the homogenization. The homogenization is, as a rule, carried out at temperatures in the range of from about 10° C. to the boiling point of the pasting agent and atmospheric pressure or slightly superatmospheric pressure. Optionally, at least one of the compounds described above can then be added. The mixture thus obtained is homogenized, preferably kneaded, until an extrudable plastic material is formed.

The homogenized mixture is then shaped to obtain a molding. All known suitable shaping methods, such as extrusion, spray drying, spray granulation, briquetting, i.e. mechanical compression with or without addition of additional binder or pelleting, i.e. compacting by circular and/or rotary movements, may be employed.

Preferred shaping methods are those in which conventional extruders are employed to shape the mixture comprising the titanium silicalite-1. Thus, for example extrudates having a diameter of from 1 to 10 mm and preferably of from 2 to 5 mm are obtained. In addition to the use of an extruder, an extrusion press can also be used for the preparation of the moldings. The shape of the moldings produced according to the invention can be chosen as desired. In particular, inter alia, spheres, oval shapes, cylinders or tablets are possible. Likewise, hollow structures, as for example hollow cylinders or honeycomb formed structures or also star-shaped geometries may be mentioned.

The shaping can take place at ambient pressure or at a pressure higher than ambient pressure, for example in a pressure range of from 1 bar to several hundred bar. Furthermore, the compacting can take place at ambient temperature or at a temperature higher than ambient temperature, for example in a temperature range of from 20 to 300° C. If drying and/or calcining are part of the shaping step, temperatures of up to 600° C. are conceivable. Finally, the compacting can take place in an ambient atmosphere or in a controlled atmosphere. Controlled atmospheres are, for example, inert gas atmospheres, reducing atmospheres and/or oxidizing atmospheres.

The shaping step is preferably followed by at least one drying step. This at least one drying step is carried out at temperatures in the range of in general from 80 to 160° C., preferably of from 90 to 145° C. and particularly preferably of from 100 to 130° C., usually for 6 h or more, for example in the range of from 6 to 24 h. However, depending on the moisture content of the material to be dried, shorter drying times, such as, for example, about 1, 2, 3, 4 or 5 h are also possible.

Before and/or after the drying step, the preferably obtained extrudate can, for example, be comminuted. Preferably granules or chips having a particle diameter of from 0.1 to 5 mm, in particular of from 0.5 to 2 mm, are obtained thereby.

According to a preferred embodiment of the present invention, the drying of the moldings, respectively, is preferably followed by at least one calcination step. Calcination is carried out at temperatures in general in the range of from 350 to 750° C., preferably form 400 to 700° C., particularly preferably from 450 to 650° C. The calcination can be effected under any suitable gas atmosphere, wherein air and/or lean air are preferred. Furthermore, the calcination is preferably carried out in a muffle furnace, a rotary kiln and/or a belt calcining furnace, wherein the duration of calcination is in general 1 h or more, for example in the range of from 1 to 24 h or in the range of from 3 to 12 h. In the process according to the invention, it is accordingly possible, for example, to calcine the catalyst shaped body once, twice or more often for in each case at least 1 h, such as, for example, in each case in the range of from 3 to 12 h, wherein it is possible for the temperatures during a calcination step to remain constant or to be changed continuously or discontinuously. If calcination is effected twice or more often, the calcination temperatures in the individual steps may be different or identical.

According to a particularly preferred embodiment, the catalyst shaped body is subjected to a hydrothermal treatment. Hydrothermal treatment can be carried out employing any suitable method known to those skilled in the art. Thus, the catalyst or catalyst shaped in general is contacted with water or water vapor. Typically, said hydrothermal treatment is carried out by charging the catalyst or according to the invention together with water into an autoclave, heating the slurry to a temperature in the range of from 100 to 200° C., preferably in the range of from 120 to 150° C. at a pressure in the range of from 1.5 to 5 bar, preferably in the range of from 2 to 3 bar, for a period in the range of from 1 to 48 hours, preferably in the range of from 24 to 48 hours. Typically at least one washing step, preferably with water as wash substance, follows. After the treatment with water the catalyst is being preferably dried and/or calcined, wherein drying and calcination is carried out as already described above. According to a preferred embodiment, the hydrothermal treatment is carried out by stirring the catalyst shaped body in an autoclave, wherein the stirring rate is adjusted to a stirring rate such that to avoid attrition as far as possible. If the catalyst is used in form of cylindrical extrudates, however, some attrition is desired to achieve cylindrical extrudates having rounded edges. With such extrudates having rounded edges, a higher bulk density can be achieved, for example for the use of the extrudates as fixed-bed catalyst in a tube reactor R1 and/or in a shaft reactor R2. Furthermore, the dust formation of said catalysts in the epoxidation process in stages (i) and (iii) is reduced.

Further, in the epoxidation process of the present invention, a titanium silicalite-1 catalyst as described above is employed, having micropores and mesopores, comprising from 49.5 to 80%, preferably 69.5 to 80% by weight of titanium silicalite-1, based on the total weight of the catalyst, and from 19.5 to 50%, preferably from 19.5 to 30% by weight of at least one binder, preferably a silica binder, based on the total weight of the catalyst shaped body.

If TS-1 is used as catalytically active material according to the present invention, it is preferred that the organic solvent is methanol.

Step (a2)

According to (a2), the feed stream according to (a1) is subjected in the reactor to epoxidation conditions in the presence of the catalyst, and a reaction mixture comprising the propylene oxide and the organic solvent is obtained.

The reactor employed in (a2) can be operated in an isothermal or in an adiabatic manner, wherein it is preferred that the reactor in (a2) is an isothermally operated reactor.

Conveniently, the conversion rate of the starting materials may be controlled by adjusting temperature, pressure, WHSV of the starting materials, and the like. By way of example, the reaction temperature may be adjusted so that at least 90% of the epoxidation agent is converted. The amounts of starting material present in the reaction mixture before and after the epoxidation reaction may be analyzed by any suitable technique, e.g. chromatography.

Generally, the continuous epoxidation reaction in (a2) can be carried out in any appropriate vessel or reactor. Preferably, the reaction in (a2) is carried out in at least one continuously operated reactor such as a tube reactor or a tube bundle reactor which preferably contains at least one cooling jacket surrounding the at least one tube, wherein the temperature of the reaction mixture is controlled isothermally using a heat transfer medium, preferably by passing the heat transfer medium through a jacket of the reactor. If the reaction in (a2) is carried out in such a reactor containing at least one cooling jacket, the term "epoxidation reaction temperature" as used herein is defined as the temperature of the heat transfer medium prior to controlling of the temperature of the reaction mixture, preferably as the temperature of the heat transfer medium at the entrance of the jacket of the isothermal reactor.

Preferably, the at least one of the reactors in which the reaction according to (a2) is carried out is a tube reactor or a tube bundle reactor.

The catalyst comprising the titanium containing zeolite can be employed in every conceivable form described hereinabove, including a powder, a micropowder, preferably a spray-powder, as a molding comprising a powder, or as a molding comprising micropowder, preferably a spray-powder. Preferably, the catalyst comprising the titanium containing zeolite of is employed as a molding comprising a powder or a micropowder, preferably a spray-powder, more preferably as a molding comprising a micropowder, preferably a spray-powder.

The catalyst used in step (a2) of the present invention can be arranged in the reactor in every conceivable manner. Preferably, the catalyst is arranged as fluidized bed or as fixed bed, more preferably as fixed bed.

Preferably, the epoxidation conditions in (a2) comprise an epoxidation reaction temperature in the range of from 20 to 100° C., more preferably from 25 to 80° C., more preferably from 25 to 60° C., more preferably from 30 to 60° C.

Preferably, the epoxidation conditions in (a2) comprise an epoxidation reaction pressure in the range of from 5 to 100 bar, more preferably from 10 to 32 bar, more preferably from 15 to 25 bar, wherein the epoxidation reaction pressure is defined as the pressure at the exit of the isothermal reactor.

Thus, the epoxidation conditions in (a2) preferably comprise an epoxidation reaction temperature in the range of from 20 to 100° C. and an epoxidation reaction pressure is in the range of from 5 to 100 bar, more preferably an epoxidation reaction temperature in the range of from 25 to 60° C. and an epoxidation reaction pressure in the range of from 10 to 32 bar, more preferably an epoxidation reaction temperature in the range of from 30 to 60° C. and an epoxidation reaction pressure in the range of from 15 to 25 bar.

The term "the epoxidation conditions" as used in this context of the present invention relate to an epoxidation reaction in step (a2) wherein for at least 98%, preferably at least 99%, more preferably at least 99.9% of the overall reaction time, the reaction temperature and pressure is in the above-defined ranges. The term "overall reaction time" as used in this context of the present invention relates to the reaction time a given catalyst bed is used before it is either discarded or subjected to regeneration. In particular at the beginning of an epoxidation reaction in (a2) when the catalyst is fresh, i.e. at the start-up of the epoxidation reaction in (a2), the reaction temperature or pressure or both can be outside the above-mentioned ranges for a short period of time. Preferably, the flow rate of the heat transfer medium is chosen so that the temperature difference between its inlet temperature and its outlet temperature is at most 3 K, more preferably at most 2 K, more preferably at most 1 K.

Preferably, the epoxidation reaction according to step (a2) of the present invention is carried out at an essentially constant epoxidation agent conversion, preferably hydrogen peroxide conversion. Preferably, in order to determine the hydrogen peroxide conversion the molar flow rate of the hydrogen peroxide in the effluent stream removed in (a3), referred to herein as $m_{out}$, is compared with the molar flow rate of hydrogen peroxide in the feed stream provided in (a1), referred to herein as $m_{in}$, and wherein the hydrogen peroxide conversion is defined as $100 \times (1-m_{out}/m_{in})$. Preferably, the inlet temperature of the heat transfer medium described above is adjusted in the above-mentioned preferred ranges in order to keep the hydrogen peroxide conversion essentially constant in the range of from 80 to 100%, more preferably from 90 to 100%, more preferably from 95 to 100%, more preferably from 99 to 100%, more preferably from 99.5 to 100%, more preferably from 99.9 to 100%. The term "the epoxidation conditions comprise" as used in this context of the present invention relate to an epoxidation reaction in step (a2) wherein for at least 98%, preferably at least 99%, more preferably at least 99.9% of the overall reaction time, the hydrogen peroxide conversion is in the above-defined ranges. The term "overall reaction time" as used in this context of the present invention relates to the reaction time a given catalyst bed is used before it is either discarded or subjected to regeneration. In particular at the beginning of an epoxidation reaction in (a2) when the catalyst is fresh, i.e. at the start-up of the epoxidation reaction in (a2), the hydrogen peroxide conversion can be outside the above-mentioned ranges for a short period of time. Preferably, the reaction temperature is not kept constant during the reaction but is adjusted continuously or step-wise to allow for a constant hydrogen peroxide conversion. Generally, due to a certain catalyst deactivation, the reaction temperature is continuously or step-wise increased. Preferably, the reaction temperature is continuously or step-wise increased by 1 K/d (Kelvin/day) at most, more preferably by less than 1 K/d.

Preferably, the reaction mixture which is present in the reactor in (a2) is liquid under the epoxidation conditions. Preferably, the reaction mixture consists of one single liquid phase, of two liquid phases, or of three or more liquid phases. Preferably, the reaction mixture in the reactor in (a2) consists of one single liquid phase or of two liquid phases, more preferably of one single liquid phase.

Generally, the reactor used in step (a2) of the present invention can be arranged horizontally or vertically. Preferably, the reactor is arranged vertically. In the preferably vertically arranged reactor, the feed stream provided in (a1) can be passed in up-flow mode or on down-flow mode, the up-flow mode being preferred. Preferably, compared with the direction of the flow of the feed stream, the heat transfer medium is passed through the jacket in co-current mode.

Generally, the epoxidation reaction in (a2) can be carried out in one or more reactors wherein these reactors can be arranged in parallel or in series. Preferably, the reaction in (a2) is carried out in one reactor or in at least two reactors, preferably two reactors, which are arranged in series wherein between two reactors arranged in series, a suitable intermediate treatment can be carried out. If the reaction is carried out in two reactors arranged in series, it is preferred that the first reactor is operated as described above, i.e. as an isothermally operated reactor, and the second reactor, i.e. the downstream reactor, is operated as adiabatic or essentially adiabatic reactor. The term "reactor" as used herein also encompasses two or more reactors arranged in parallel wherein a feed stream passed is divided in two or more sub-streams, each substream is passed into a reactor, and the effluent streams removed from the reactors are combined to obtain the overall effluent stream. Therefore, the epoxidation reaction can be carried out in at least one first reactor such as two or more first reactors, for example 2, 3, 4 first reactors, which are arranged in parallel and which are preferably isothermal reactors, and in at least one second reactor such as two or more second reactors, for example 2, 3, 4 second reactors, which are arranged in parallel and which are preferably adiabatic or essentially adiabatic reactors.

If the epoxidation reaction according to (a2) is carried out in two reactors arranged in series, it is preferred that in the first reactor which is preferably an isothermally operated reactor, the hydrogen peroxide conversion is kept essentially constant in a range of from 80 to 99%, preferably from 85 to 98%, more preferably from 90 to 97%, and in the second reactor which is preferably designed as adiabatic or essentially adiabatic reactor, the overall hydrogen peroxide conversion, i.e. the hydrogen peroxide conversion taking into account the conversion in the first and the second reactor, is brought to a value of more than 99%, preferably at least 99.5%, more preferably at least 99.9%.

Step (a3)

According to step (a3), a product stream comprising the propylene oxide and the organic solvent is removed from the reactor. Said product stream is typically subjected to at least one work-up step to isolate the propylene oxide from the product stream. Further, the organic solvent, which typically comprises side products of the epoxidation reaction, is preferably subjected to one or more work-up steps to allow recirculation of the organic solvent, preferably acetonitrile, preferably after one or more purification steps into step (a1). A preferred sequence of work-up steps is described in Reference Example 2 and in FIGS. 1 and 2 hereinbelow.

Step (b)

According to (b), introducing the feed stream into the reactor according to (a1) is stopped.

Preferably, step (b) further comprises separating the reaction mixture comprising propylene oxide and the organic solvent from the catalyst comprising the titanium containing zeolite as catalytically active material. This separation of the reaction mixture from the spent catalyst comprising a titanium containing zeolite can be achieved in any suitable manner, such as pumping, draining, decanting, filtrating, and the like. Optionally, (b) further comprises drying the catalyst before carrying out the washing in (c), wherein preferably the catalyst is not dried before carrying out the washing in (c). If drying is carried out, it is preferred that said drying includes bringing the catalyst in contact with a gas stream comprising nitrogen, preferably at a temperature of said gas stream in the range of from 40 to 200° C., more preferably in the range of from 55 to 150° C., more preferably in the range of from 70 to 100° C. Said separation can further be achieved by flushing the reactor with the organic solvent, preferably acetonitrile.

Thus, in a preferred embodiment, the reactor is flushed free of hydrogen peroxide, propylene and propylene oxide by replacing the feed stream according to (a1) by a stream essentially consisting of the organic solvent, preferably of acetonitrile until the reactor is essentially free of hydrogen peroxide, propylene and propylene oxide and optionally depressurizing and emptying the reactor. For example, a stream essentially consisting of the organic solvent, preferably of acetonitrile, contains at least 60 weight-%, preferably at least 70 weight-%, more preferably at least 75 weight-%, more preferably at least 80 weight-% of the organic solvent, and optionally contains at least one further liquid, preferably comprising water. Therefore, it is preferred that at least 95 weight-%, more preferably at least 98 weight-%, more preferably at least 99 weight-% of the stream essentially consisting of the organic solvent, preferably of acetonitrile, consist of the organic solvent, preferably acetonitrile, and water, wherein at least 60 weight-%, preferably at least 70 weight-%, more preferably at least 75 weight-%, more preferably at least 80 weight-% of the stream consist of the organic solvent, preferably acetonitrile. Said flushing is preferably carried out a temperature of said stream essentially consisting of the organic solvent, preferably of acetonitrile, in the range of from 20 to 90° C., more preferably in the range of from 25 to 80° C., more preferably in the range of from 30 to 70° C.

In an alternative preferred embodiment, the present process further comprises preparing the feed stream in (a1) by mixing a stream comprising the propene, a stream comprising the hydrogen peroxide or the hydrogen peroxide source, and a stream comprising the organic solvent, wherein step (b) comprises (b1) stopping the stream comprising the hydrogen peroxide or the hydrogen peroxide source;
(b2) stopping the stream comprising the propene and the stream comprising the organic solvent;
(b3) optionally depressurizing and emptying the reactor,
wherein step (b2) is carried out preferably at least 30 min, more preferably at least 60 min, after step (b1).

Step (c)

According to step (c), the catalyst is washed with a liquid aqueous system.

The possible components of the liquid aqueous system according to (c) and the respective amounts thereof as described hereinafter are to be understood as regarding the liquid aqueous system employed in (c) prior to the addition to the catalyst comprising a titanium containing zeolite.

Generally, the liquid aqueous system according to (c) is not restricted with regard to the amount of water contained therein. The liquid aqueous system may thus contain for example at least 50 weight-%, or at least 75 weight-%, or at least 85 weight-% water, based on the total weight of the liquid aqueous system. Preferably, the liquid aqueous system according to (c) contains at least 95 weight-%, more preferably at least 99 weight-%, more preferably at least 99.9 weight-%, more preferably at least 99.99 weight-% water based on the total weight of the liquid aqueous system.

The water employed in (c) may be obtained from any suitable source. Preferably, the water employed in (c) is demineralized water or condensate.

Preferably, the liquid aqueous system according to (c) contains methanol only in minor amounts, while it is preferably free or at least essentially free of methanol. Preferably, the liquid aqueous system according to (c) contains at most 5 weight-%, more preferably 1 weight-%, more preferably 0.1 weight-%, more preferably 0.01 weight-%, more preferably 0.001 weight-%, more preferably 0.0001 weight-% methanol, based on the total weight of the liquid aqueous system.

Preferably, the liquid aqueous system according to (c) contains hydrogen peroxide only in minor amounts, while it is preferably free or at least essentially free of methanol. Preferably, the liquid aqueous system according to (c) contains at most 0.1 weight-%, preferably 0.01 weight-%, more preferably 0.001 weight-%, more preferably 0.0001 weight-% hydrogen peroxide, based on the total weight of the liquid aqueous system.

Preferably, the liquid aqueous system according to (c) has a pH value of from 4 to 10, preferably from 7 to 9 as determined with a pH electrode.

Particularly preferably, the liquid aqueous system according to (c) consists of water.

The washing in (c) can be carried out in any conceivable container. Thus, the washing can be carried out for example in the reactor containing the catalyst or in any another suitable vessel in case that the catalyst is removed from the reactor for the washing in (c). Preferably, the washing in (c) is carried out in the reactor containing the catalyst.

Thus, the washing in (c) is preferably carried out in the reactor containing the catalyst, wherein the liquid aqueous system according to (c) contains at least 95 weight-%, preferably at least 99 weight-%, more preferably at least 99.9 weight-%, more preferably at least 99.99 weight-% water, based on the total weight of the liquid aqueous system.

The washing in (c) can performed either in batch mode or in continuous mode. In case that the washing is performed in batch mode, the catalyst is contacted one or several times with a specific amount of the liquid aqueous system. The washing may thus be performed by immersing the catalyst in the liquid aqueous system. During the washing it is possible to subject the liquid aqueous system together with the catalyst to stirring. It is conceivable that when the washing in (c) is performed in batch mode, the liquid aqueous system may be replaced one or more times.

In case that the washing is performed in continuous mode, the catalyst is continuously contacted with a stream of the liquid aqueous system. In case that the reactor comprising the catalyst is arranged vertically and the washing is performed in the reactor or that the washing is carried out outside the reactor in any another suitable vertically arranged vessel, the washing may be performed either in upflow or downflow mode, preferably in downflow mode. Preferably, the washing in (c) is carried out in continuous mode. More preferably, the washing in (c) is carried out in continuous mode in the reactor containing the catalyst.

Thus, the washing in (c) is preferably carried out in continuous mode in the reactor containing the catalyst, wherein the liquid aqueous system according to (c) contains at least 95 weight-%, preferably at least 99 weight-%, more preferably at least 99.9 weight-%, more preferably at least 99.99 weight-% water, based on the total weight of the liquid aqueous system.

Preferably, the washing in continuous mode is performed in a tube reactor or a tube bundle reactor with the liquid aqueous system having a liquid hourly space velocity (LHSV) in the range of from 1 to 20 m/h, more preferably from 5 to 15 m/h, more preferably from 5 to 10 m/h. The liquid hourly space velocity LHSV in (c) is defined as the volume flow rate of the liquid aqueous system in cubic meters per hour divided by the total cross section in square meters of the empty tube of the reactor or the empty tubes of the reactor in case a tube bundle reactor is used, wherein the tube has a constant diameter over its entire length and the tubes have constant diameters over their entire length, respectively.

Thus, the washing in (c) is preferably carried out in continuous mode in a tube reactor or a tube bundle reactor containing the catalyst, wherein the liquid aqueous system contains at least 95 weight-%, preferably at least 99 weight-%, more preferably at least 99.9 weight-%, more preferably at least 99.99 weight-% water, based on the total weight of the liquid aqueous system, and it is performed with the liquid aqueous system having a LHSV in the range of from 1 to 20 m/h, more preferably from 5 to 15 m/h, more preferably from 5 to 10 m/h.

The washing in (c) can be performed at any suitable temperature of the liquid aqueous system.

Preferably, the washing in (c) is performed at a temperature of the liquid aqueous system in the range of from 30 to 90° C., preferably from 40 to 80° C.

The washing in (c) can be performed for any time needed to achieve a sufficient washing of the catalyst employed in (a2). Preferably, the washing in (c) is performed for 1 to 25 hours, preferably from 1.5 to 20 hours, more preferably from 2 to 12 hours, more preferably from 2.5 to 9 hours, more preferably from 3 to 6 hours.

Thus, the washing in (c) is preferably performed at a temperature of the liquid aqueous system in the range of from 30 to 90° C. for 2.5 to 9 hours, more preferably at a temperature of the liquid aqueous system in the range of from 40 to 80° C. for 3 to 6 hours.

Thus, the washing in (c) is preferably carried out in continuous mode in a tube reactor or a tube bundle reactor containing the catalyst, wherein the liquid aqueous system contains at least 95 weight-%, preferably at least 99 weight-%, more preferably at least 99.9 weight-%, more preferably at least 99.99 weight-% water, based on the total weight of the liquid aqueous system, and it is performed with the liquid aqueous system having a LHSV in the range of from 5 to 15 m/h at a temperature of the liquid aqueous system in the range of from 30 to 90° C. for 2.5 to 9 hours, more preferably from 5 to 10 m/h at a temperature of the liquid aqueous system in the range of from 40 to 80° C. for 3 to 6 hours.

According to the present process, the washing in (c) is typically monitored by the total organic carbon concentration of the liquid aqueous system after having been contacted with the catalyst, and the washing in (c) is preferably performed until a specific total organic carbon concentration of the liquid aqueous system after having been contacted with the catalyst is reached. As the total organic carbon concentration passes through a maximum during the washing in (c), the specific concentration which is preferably reached refers to the value reached after passing the maximum.

Preferably the washing in (c) is performed until the total organic carbon concentration of the liquid aqueous system after having been contacted with the catalyst is 25% or less, preferably 20% or less, preferably 15% or less, preferably 10% or less, more preferably 5% or less, more preferably 4% or less, more preferably 3% or less, more preferably 2% or less, more preferably 1% or less of the maximum total organic carbon concentration detected during the washing in (c), wherein the total volume of the liquid aqueous system is equal to or larger than the inner volume of the reactor. The total organic carbon concentration is understood as being determined according to DIN EN 1484.

The point in time when step (b) is carried out and introducing the feed stream into the reactor is stopped to allow the washing in (c) is preferably chosen based on the decrease of the selectivity regarding the formation of propylene oxide in (a2) relative to the average selectivity of the reaction in (a2) during the first 100 h of carrying out step (a). The selectivity regarding the formation of propylene oxide in (a2) in the context of the present process is understood as the selectivity regarding the formation of propylene oxide in (a2) based on hydrogen peroxide and calculated as shown in comparative example 1. Thus, step (b) may be carried out for example when the selectivity regarding the formation of propylene oxide in (a2) has decreased by 15% or less, or by 10% or less, or by 6% or less relative to the average selectivity of the reaction in (a2) during the first 100 h of carrying out step (a). Preferably, step (b) is carried out when the selectivity regarding the formation of propylene oxide in (a2) has decreased by 4% or less, preferably by 3% or less, more preferably by 2% or less relative to the average selectivity of the reaction in (a2) during the first 100 h of carrying out step (a).

Stage (i) further comprises repeating the sequence of steps (a) to (c) n times with n being an integer and being at least 1. Thus, the sequence of steps (a) to (c) is repeated at least once before stage (ii) is carried out. Preferably, n is in the range of from 1 to 10 and thus 1, 2, 3, 4, 5, 6, 7, 8, 9, or 10. More preferably, n is in the range of from 1 to 6 and thus 1, 2, 3, 4, 5, or 6. More preferably, n is in the range of from 1 to 4 and thus 1, 2, 3, or 4.

According to the present process, the catalyst obtained from (b) is preferably washed only with one liquid aqueous system containing at least 95 weight-%, more preferably at least 99 weight-%, more preferably at least 99.9 weight-%, more preferably at least 99.99 weight-% water based on the total weight of the liquid aqueous system. This washing is preferably carried out in continuous mode. Thus, it is preferred that the catalyst is treated with no other liquid system between step (b) and stage (ii) except the liquid aqueous system containing at least 95 weight-%, more preferably at least 99 weight-%, more preferably at least 99.9 weight-%, more preferably at least 99.99 weight-% water based on the total weight of the liquid aqueous system. Thus, preferably, not pre- or after-treatment with a different liquid aqueous system, preferably with any different liquid system is carried out, wherein the flushing of the reactor with the organic solvent, preferably acetonitrile in (b) is not excluded by this preferred embodiment.

According to the present process, the catalyst obtained from (b) is preferably not treated with a gas stream consisting of, preferably comprising ozone.

Optionally, (c) further comprises drying the washed catalyst. If drying is carried out, it is preferred that said drying includes bringing the catalyst in contact with a gas stream comprising nitrogen, preferably at a temperature of said gas stream in the range of from 40 to 200° C., more preferably in the range of from 55 to 150° C., more preferably in the range of from 70 to 100° C. According to the present invention, it is preferred that said drying is not carried after a washing step (c) after which no calcination is carried out, i.e. is carried out after the very washing step (c) after which stage (ii) is carried out.

Stage (ii)

The present process for the regeneration further comprises
(ii) a stage comprising calcining the catalyst obtained from
(c) after having repeated the sequence of steps (a) to (c) n times.

Preferably, the calcining in (ii) is performed at a temperature of the catalyst bed in the range of from 300 to 600° C., preferably from 350 to 550° C., more preferably from 400 to 500° C.

The calcining in (ii) can be performed in a static surrounding gas atmosphere or in a gas stream with which the catalyst is brought into contact. Preferably, the calcining in (ii) is performed in a gas stream. Generally, said gas stream is not restricted with regard to the components present therein. Preferably, said gas stream comprises oxygen, preferably oxygen and nitrogen. Generally, said gas stream comprising oxygen, preferably oxygen and nitrogen is not restricted with regard to the source used for the oxygen, preferably oxygen and nitrogen. Preferably air, lean air, or a mixture thereof, more preferably air or lean air is used as a source. Thus, the calcining in (ii) is preferably performed in a gas stream comprising oxygen, preferably oxygen and nitrogen, wherein the gas stream comprising oxygen, preferably oxygen and nitrogen, is preferably air, lean air, or a mixture thereof, more preferably air or lean air.

Thus, the calcining in (ii) is preferably performed at a temperature of the catalyst bed in the range of from 300 to 600° C., preferably from 350 to 550° C., more preferably from 400 to 500° C. in a gas stream comprising oxygen, preferably oxygen and nitrogen, wherein the gas stream comprising oxygen, preferably oxygen and nitrogen, is preferably air, lean air, or a mixture thereof, more preferably air or lean air.

The calcining in (ii) can be performed for any time needed to achieve a sufficient calcination of the catalyst in the present process for the regeneration of a catalyst. Preferably, the calcining in (ii) is performed for 1 to 15 hours, preferably from 2 to 10 hours, more preferably from 3 to 7 hours.

Thus, the calcining in (ii) is preferably performed at a temperature of the catalyst bed in the range of from 300 to 600° C. for 1 to 15 hours, more preferably from 350 to 550° C. for 2 to 10 hours, more preferably from 400 to 500° C. from 3 to 7 hours in a gas stream comprising oxygen, preferably oxygen and nitrogen, wherein the gas stream comprising oxygen, preferably oxygen and nitrogen, is preferably air, lean air, or a mixture thereof, more preferably air or lean air.

The calcining in (ii) can be carried out in any conceivable container. Thus, the calcining in (ii) can be carried out for example in the reactor containing the catalyst or in any another suitable vessel, in case that the catalyst is removed from the reactor for the calcining in (ii). Preferably, the calcining in (ii) is carried out in the reactor containing the catalyst.

The sequence of stages (i) and (ii) of the present process for the regeneration of a catalyst may be repeated m times before the catalyst is discarded with m being an integer and being at least 1, wherein in each repetition of the sequence of stages (i) and (ii), n is the same or different. Thus, the sequence of stages (i) and (ii) is repeated at least once wherein in each repetition of the sequence of stages (i) and (ii), n is the same or different. Preferably, m is in the range of from 1 to 10 and thus 1, 2, 3, 4, 5, 6, 7, 8, 9, or 10. More preferably, m is in the range of from 1 to 6 and thus 1, 2, 3, 4, 5, or 6. More preferably, m is in the range of from 1 to 4 and thus 1, 2, 3, or 4.

Preferably, m is 1, 2, 3, 4, 5, 6, 7, 8, 9, or 10 while n is 1, 2, 3, 4, 5, 6, 7, 8, 9, or 10, more preferably 1, 2, 3, 4, 5, or 6, more preferably 1, 2, 3, or 4. More preferably, m is 1, 2, 3, 4, 5, or 6 while n is 1, 2, 3, 4, 5, 6, 7, 8, 9, or 10, more preferably 1, 2, 3, 4, 5, or 6, more preferably 1, 2, 3, or 4.

More preferably, m is 1, 2, 3, or 4 while n is 1, 2, 3, 4, 5, 6, 7, 8, 9, or 10, more preferably 1, 2, 3, 4, 5, or 6, more preferably 1, 2, 3, or 4.

The Regenerated Catalyst

The present invention further relates to a regenerated catalyst comprising a titanium containing zeolite as catalytically active material, obtainable or obtained by a process according to the present invention and as described hereinabove.

It is preferred that the catalyst regenerated according to the present invention exhibits in a process for the preparation of propylene oxide a differential conversion temperature of at most 5 K, preferably at most 2 K, more preferably at most 1 K, wherein the differential conversion temperature is defined as the absolute difference between
(A1) the temperature at which a pre-determined conversion of the hydrogen peroxide is achieved in said process for the preparation of propylene oxide in which the regenerated catalyst is used as catalyst, and
(B1) the temperature at which said pre-determined conversion of the hydrogen peroxide is achieved in said process for the preparation of propylene oxide in which the respective fresh catalyst is used as catalyst under otherwise identical epoxidation reaction conditions.

After a certain operation time a decrease in the catalytic activity of a catalyst comprising a titanium containing zeolite as catalytically active material is observed in an epoxidation reaction. The reduced catalytic activity is directly related to a reduced conversion rate for at least one of the starting materials, i.e., the olefin and/or the epoxidation agent, wherein the reduced conversion rate may be compensated by increasing the overall reaction temperature. This implies that with continued operation of the catalyst a gradual increase of the reaction temperature is required relative to the starting temperature, making the epoxidation process increasingly ineffective.

However, by subjecting a catalyst comprising a titanium containing zeolite spent in an epoxidation reaction to the regeneration process of the present invention, its initial catalytic activity may be restored. The initial catalytic activity refers here to the catalytic activity of a freshly prepared catalyst. Since the catalytic activity is conveniently directly related to the reaction temperature under otherwise identical reaction conditions, the efficiency of a regeneration of a spent catalyst may be deduced from the reaction temperature required to maintain a set conversion rate. In the present case, the catalyst regenerated according to the present invention favorably exhibits in the process for the preparation of an olefin oxide, a conversion temperature which deviates by at most 5 K, preferably at most 2 K, more preferably at most 1 K from the conversion temperature of fresh catalyst under otherwise identical epoxidation conditions.

It is further preferred that the catalyst regenerated according to the process of the present invention exhibits in a process for the preparation of propylene oxide, a differential selectivity of at most 1, wherein the differential selectivity is defined as the absolute difference in % points between
(A2) the selectivity based on the hydrogen peroxide in said process for the preparation of propylene oxide in which the regenerated catalyst is used as catalyst, and
(B2) the selectivity based on the hydrogen peroxide in said process for the preparation of propylene oxide in which the respective fresh catalyst is used as catalyst under otherwise identical epoxidation reaction conditions, wherein the selectivity based on the hydrogen peroxide is defined as moles of propylene oxide produced divided by moles of hydrogen peroxide consumed×100.

The quality of the catalyst comprising a titanium containing zeolite regenerated according to the process of the present invention may also be quantified by comparing the selectivity of the regenerated catalyst with the selectivity of fresh catalyst under otherwise identical epoxidation conditions. Following a prolonged use also a decrease of the selectivity of the catalyst is typically observed. Favorably, in the present case, after having been submitted to the regeneration process of the present invention, a catalyst comprising a titanium containing zeolite has a selectivity which deviates by at most 1 percentage points from the selectivity of fresh catalyst under otherwise identical epoxidation reaction conditions.

The continuous process for the preparation of propylene oxide

According to the present invention, it is preferred that the epoxidation reaction is carried out in more than one reactor, for example in at least two reactors, three reactors, or four reactors, which reactors are operated in parallel. According to this process design, it is preferred that during the regeneration of the catalyst in a given reactor, the epoxidation reaction is carried out in one or more of the remaining reactors. Thus, propylene oxide can be prepared in a continuous manner and simultaneously, the inventive regeneration can be carried out. It can be preferred that according to this process design, the epoxidation reaction in the at least two reactors is started sequentially with a suitable delay between the respective start-ups.

The present invention further relates to a continuous process for the preparation of propylene oxide, comprising
(i') a stage comprising
  (a') continuously preparing propylene oxide in a first reactor comprising
    (a1') introducing a feed stream comprising propene, hydrogen peroxide or a hydrogen peroxide source, and an organic solvent into the first reactor containing a catalyst comprising a titanium containing zeolite as catalytically active material;
    (a2') subjecting the feed stream according to (a1') in the first reactor to epoxidation conditions in the presence of the catalyst, obtaining a reaction mixture comprising the propylene oxide and the organic solvent;
    (a3') removing a product stream comprising the propylene oxide and the organic solvent from the first reactor;
  (b') stopping introducing the feed stream into the first reactor;
  (c') washing the catalyst with a liquid aqueous system;
  stage (i') further comprising repeating the sequence of steps (a') to (c') n' times with n' being an integer and being at least 1; the process the preparation of propylene oxide further comprising
(ii') a stage comprising calcining the catalyst obtained from (c') after having repeated the sequence of steps (a') to (c') n' times;
wherein the sequence of stages (i') to (ii') is optionally repeated m' times with m' being an integer and being at least 1, wherein in each repetition of the sequence of steps (i') to (ii'), n' is the same or different;
the process for the preparation of propylene oxide further comprising
(i") a stage comprising
  (a") continuously preparing propylene oxide in a second reactor comprising
    (a1") introducing a feed stream comprising propene, hydrogen peroxide or a hydrogen peroxide source, and an organic solvent into the second reactor containing a catalyst comprising a titanium containing zeolite as catalytically active material;

(a2") subjecting the feed stream according to (a1") in the second reactor to epoxidation conditions in the presence of the catalyst, obtaining a reaction mixture comprising the propylene oxide and the organic solvent;

(a3") removing a product stream comprising the propylene oxide and the organic solvent from the second reactor;

(b") stopping introducing the feed stream into the second reactor;

(c") washing the catalyst with a liquid aqueous system;

stage (i") further comprising repeating the sequence of steps (a") to (c") n" times with n" being an integer and being at least 1; the process the preparation of propylene oxide further comprising (ii") a stage comprising calcining the catalyst obtained from (c") after having repeated the sequence of steps (a") to (c") n" times;

wherein the sequence of stages (i") to (ii") is optionally repeated m" times with m" being an integer and being at least 1, wherein in each repetition of the sequence of steps (i") to (ii"), n" is the same or different;

wherein during at least one sequence of steps (b') and (c') or at least one sequence of steps (b'), (c') and (ii'), propylene oxide is prepared according to (a").

The present invention is further characterized by the following embodiments and combinations of embodiments indicated by the respective dependencies:

1. A process for the regeneration of a catalyst comprising a titanium containing zeolite as catalytically active material, comprising
   (i) a stage comprising
      (a) continuously preparing propylene oxide comprising
         (a1) introducing a feed stream comprising propene, hydrogen peroxide or a hydrogen peroxide source, and an organic solvent into a reactor containing a catalyst comprising the titanium containing zeolite as catalytically active material;
         (a2) subjecting the feed stream according to (a1) in the reactor to epoxidation conditions in the presence of the catalyst, obtaining a reaction mixture comprising the propylene oxide and the organic solvent;
         (a3) removing a product stream comprising the propylene oxide and the organic solvent from the reactor;
      (b) stopping introducing the feed stream into the reactor;
      (c) washing the catalyst with a liquid aqueous system;
      stage (i) further comprising repeating the sequence of steps (a) to (c) n times with n being an integer and being at least 1; the process for the regeneration further comprising
   (ii) a stage comprising calcining the catalyst obtained from (c) after having repeated the sequence of steps (a) to (c) n times;
   wherein the sequence of stages (i) to (ii) is optionally repeated m times with m being an integer and being at least 1, wherein in each repetition of the sequence of stages (i) to (ii), n is the same or different.

2. The process of embodiment 1, comprising preparing the feed stream according to (a1) by mixing a stream comprising the propene, a stream comprising the hydrogen peroxide or the hydrogen peroxide source, and a stream comprising the organic solvent.

3. The process of embodiment 2, wherein the feed steam according to (a1) further comprises at least one potassium comprising salt.

4. The process of embodiment 2, wherein the at least one potassium comprising salt o is one or more of potassium dihydrogen phosphate, dipotassium hydrogen phosphate, and potassium formate.

5. The process of embodiment 3 or 4, wherein preparing the feed stream according to (a1) comprises combining an aqueous stream comprising the at least one dissolved potassium comprising salt with the stream comprising the propene, or with the stream comprising the hydrogen peroxide or the hydrogen peroxide source, or with the stream comprising the organic solvent, or with a mixed stream of two or three of these streams, preferably with the stream comprising the hydrogen peroxide or the hydrogen peroxide source, or with the stream comprising the organic solvent, or with a mixed stream thereof.

6. The process of any of embodiments 1 to 5, wherein the organic solvent is methanol or acetonitrile, preferably acetonitrile.

7. The process of any of embodiments 1 to 6, wherein the molar ratio of propene relative to hydrogen peroxide or relative to hydrogen peroxide resulting from the hydrogen peroxide source in the feed stream according to (a1) is in the range of from 1:1 to 1.6:1, preferably from 1.1:1 to 1.55:1, more preferably from 1.2:1 to 1.5:1, more preferably from 1.30:1 to 1.45:1.

8. The process of any of embodiments 1 to 7, wherein the reactor according to (a2) is an isothermally operated reactor.

9. The process of any of embodiments 1 to 8, wherein according to (a2), the temperature of the reaction mixture is controlled isothermally using a heat transfer medium, preferably by passing the heat transfer medium through a jacket of the reactor.

10. The process of embodiment 9, wherein the epoxidation conditions according to (a2) comprise an epoxidation reaction temperature in the range of from 20 to 100° C., preferably from 25 to 80° C., more preferably from 30 to 60° C., wherein the epoxidation reaction temperature is defined as the temperature of the heat transfer medium prior to controlling of the temperature of the reaction mixture, preferably as the temperature of the heat transfer medium at the entrance of the jacket of the isothermally operated reactor.

11. The process of any of embodiments 1 to 10, wherein the epoxidation conditions in (a2) comprise an epoxidation reaction pressure in the range of from 5 to 100 bar, preferably from 10 to 32 bar, more preferably from 15 to 25 bar, wherein the epoxidation reaction pressure is defined as the pressure at the exit of the isothermally operated reactor.

12. The process of any of embodiments 1 to 11, wherein the titanium containing zeolite has an MFI framework structure, an MEL framework structure, an MWW framework structure, an MWW-type framework structure, or a mixed structure of two or more of these framework structures, preferably an MFI framework structure, an MWW framework structure or an MWW-type framework structure, more preferably an MWW framework structure or an MWW-type framework structure.

13. The process of any of embodiments 1 to 12, wherein at least 99 weight-%, preferably at least 99.5 weight-%, more preferably at least 99.9 weight-% the framework structure of the titanium containing zeolite consist of silicon, titanium, and oxygen.

14. The process of any of embodiments 1 to 13, wherein the titanium containing zeolite comprises one or more of Al, B, Zr, V, Nb, Ta, Cr, Mo, W, Mn, Fe, Co, Ni, Zn, Ga, Ge, In, Sn, Pb, Pd, Pt, Au, Cd, preferably one or more of B, Zr, V, Nb, Ta, Cr, Mo, W, Mn, Fe, Co, Ni, Zn, Ga, Ge, In, Sn, Pb, Pd, Pt, Au, Cd, more preferably Zn.
15. The process of embodiment 14, wherein the titanium containing zeolite which is comprised in the catalyst according to (a2) has an MWW framework structure, comprises zinc, and comprises the titanium, calculated as elemental titanium, in an amount in the range of from 0.1 to 5 weight-%, preferably from 1 to 2 weight-%, based on the total weight of the titanium containing zeolite, and comprises the zinc, calculated as elemental zinc, in an amount in the range of from 0.1 to 5 weight-%, preferably from 1 to 2 weight-%, based on the total weight of the titanium containing zeolite.
16. The process of any of embodiments 1 to 15, wherein the catalyst comprising a titanium containing zeolite is present in the reactor as fixed-bed catalyst.
17. The process of any of embodiments 1 to 16, wherein the catalyst comprising a titanium containing zeolite is present in the reactor as molding comprising the titanium containing zeolite, wherein the molding preferably comprises the titanium containing zeolite in an amount in the range of from 70 to 80 weight-% and a binder in an amount in the range of from 30 to 20 weight-%, based on the total weight of the molding, wherein the binder is preferably a silica binder.
18. The process of any of embodiments 1 to 17, comprising preparing the feed stream according to (a1) by mixing a stream comprising the propene, a stream comprising the hydrogen peroxide or the hydrogen peroxide source, and a stream comprising the organic solvent, wherein for stopping introducing the feed stream into the reactor according to (b), preparing the feed stream according to (a1) comprises
    (a11) stopping the stream comprising the hydrogen peroxide or the hydrogen peroxide source and maintaining mixing the stream comprising the propene and the stream comprising the organic solvent to obtain the feed stream;
    (a12) stopping the stream comprising the propene and the stream comprising the organic solvent;
    wherein (a11) is carried out preferably at least 30 min, more preferably at least 60 min, after (a12), and wherein, after (a12), the reactor is optionally depressurized and emptied
19. The process of any of embodiments 1 to 18, wherein the liquid aqueous system according to (c) contains at least 95 weight-%, preferably at least 99 weight-%, more preferably at least 99.9 weight-%, more preferably at least 99.99 weight-% water, based on the total weight of the liquid aqueous system.
20. The process of any of embodiments 1 to 19, wherein the liquid aqueous system according to (c) contains at most 5 weight-%, preferably at most 1 weight-%, more preferably at most 0.1 weight-%, more preferably at most 0.01 weight-%, more preferably at most 0.001 weight-%, more preferably at most 0.0001 weight-% methanol, based on the total weight of the liquid aqueous system.
21. The process of any of embodiments 1 to 20, wherein the liquid aqueous system according to (c) contains at most 0.1 weight-%, preferably at most 0.01 weight-%, more preferably at most 0.001 weight-%, more preferably at most 0.0001 weight-% hydrogen peroxide, based on the total weight of the liquid aqueous system.
22. The process of any of embodiments 1 to 21, wherein according to (c), the washing of the catalyst is carried out in the reactor containing the catalyst.
23. The process of any of embodiments 1 to 22, wherein the total volume of the liquid aqueous system used according to (c) is equal to or higher than the inner volume of the reactor.
24. The process of any of embodiments 1 to 23, wherein the washing according to (c) is performed in continuous mode.
25. The process of embodiment 24, wherein the reactor according to (a) is a tube reactor or a tube bundle reactor and the washing according to (c) is performed with the liquid aqueous system at a liquid hourly space velocity (LHSV) in the range of from 1 to 20 m/h, preferably from 5 to 15 m/h, more preferably from 5 to 10 m/h.
26. The process of any of embodiments 1 to 25, wherein the washing according to (c) is performed at a temperature of the liquid aqueous system in the range of from 30 to 90° C., preferably from 40 to 80° C.
27. The process of any of embodiments 1 to 26, wherein the washing according to (c) is performed for 1 to 25 hours, preferably for 1.5 to 20 hours, more preferably for 2 to 12 hours, more preferably for 2.5 to 9 hours, more preferably for 3 to 6 hours.
28. The process of any of embodiments 1 to 27, wherein the washing according to (c) is performed until the total organic carbon concentration of the liquid aqueous system after having been contacted with the catalyst is at most 25%, preferably at most 20%, preferably at most 15%, preferably at most 10%, more preferably at most 5%, more preferably at most 1% of the maximum total organic carbon concentration detected during the washing in (c).
29. The process of any of embodiments 1 to 28, wherein the sequence of steps (b) and (c) is carried out when the selectivity of the epoxidation reaction according to (a2) has decreased by 4%, preferably by 3%, more preferably by 2%, relative to the average selectivity of the expodation reaction according to (a2) during the first 100 h of carrying out step (a), wherein the selectivity of the epoxidation reaction is defined as the molar amount of propylene oxide obtained in (a2) relative to the molar amount of hydrogen peroxide converted in (a2).
30. The process of any of embodiments 1 to 29, wherein n is in the range of from 1 to 10, preferably from 1 to 6, more preferably from 1 to 4.
31. The process of any of embodiments 1 to 30, wherein the calcining according to stage (ii) is performed at a temperature of the catalyst in the range of from 300 to 600° C., preferably from 350 to 550° C., more preferably from 400 to 500° C.
32. The process of any of embodiments 1 to 31, wherein the calcining according to stage (ii) is performed using a gas stream comprising oxygen, preferably oxygen and nitrogen, wherein the gas stream is preferably air, lean air, or a mixture thereof, more preferably air or lean air.
33. The process of any of embodiments 1 to 32, wherein the calcining according to stage (ii) is performed for 1 to 15 hours, preferably from 2 to 10 hours, more preferably from 3 to 7 hours.
34. The process of any of embodiments 1 to 33, wherein the calcining according to stage (ii) is carried out in the reactor containing the catalyst.
35. The process of any of embodiments 1 to 34, wherein the sequence of stages (i) to (ii) is repeated m times with m being an integer the range of from 1 to 10, preferably from 1 to 6, more preferably from 1 to 4.

36. A regenerated catalyst comprising a titanium containing zeolite as catalytically active material, obtainable or obtained by a process according to any of embodiments 1 to 35.

37. The regenerated catalyst of embodiment 36, wherein the titanium containing zeolite has an MWW framework structure, wherein at least 99 weight-%, preferably at least 99.5 weight-%, more preferably at least 99.9 weight-% the framework structure of the titanium containing zeolite consist of silicon, titanium, and oxygen, wherein the titanium containing zeolite preferably comprises Zn, and wherein the titanium containing zeolite comprises the titanium, calculated as elemental titanium, in an amount in the range of from 0.1 to 5 weight-%, preferably from 1 to 2 weight-%, based on the total weight of the titanium containing zeolite, and preferably comprises the zinc, calculated as elemental zinc, in an amount in the range of from 0.1 to 5 weight-%, preferably from 1 to 2 weight-%, based on the total weight of the titanium containing zeolite.

38. The regenerated catalyst of embodiment 36 or 37, wherein the regenerated catalyst is a molding comprising the titanium containing zeolite, wherein the molding preferably comprises the titanium containing zeolite in an amount in the range of from 70 to 80 weight-% and a binder in an amount in the range of from 30 to 20 weight-%, based on the total weight of the molding, wherein the binder is preferably a silica binder.

39. The regenerated catalyst of any of embodiments 36 to 38, exhibiting, in a process for the preparation of propylene oxide, a differential conversion temperature of at most 5 K, preferably at most 2 K, more preferably at most 1 K, wherein the differential conversion temperature is defined as the absolute difference between
   (A1) the temperature at which a pre-determined conversion of the hydrogen peroxide is achieved in said process for the preparation of propylene oxide in which the regenerated catalyst is used as catalyst, and
   (B1) the temperature at which said pre-determined conversion of the hydrogen peroxide is achieved in said process for the preparation of propylene oxide in which the respective fresh catalyst is used as catalyst under otherwise identical epoxidation reaction conditions.

40. The regenerated catalyst of any of embodiments 36 to 39, exhibiting, in a process for the preparation of propylene oxide, a differential selectivity of at most 1, wherein the differential selectivity is defined as the absolute difference in % points between
   (A2) the selectivity based on the hydrogen peroxide in said process for the preparation of propylene oxide in which the regenerated catalyst is used as catalyst, and
   (B2) the selectivity based on the hydrogen peroxide in said process for the preparation of propylene oxide in which the respective fresh catalyst is used as catalyst under otherwise identical epoxidation reaction conditions, wherein the selectivity based on the hydrogen peroxide is defined as moles of propylene oxide produced divided by moles of hydrogen peroxide consumed×100.

41. A continuous process for the preparation of propylene oxide, comprising
   (i') a stage comprising
      (a') continuously preparing propylene oxide in a first reactor comprising
         (a1') introducing a feed stream comprising propene, hydrogen peroxide or a hydrogen peroxide source, and an organic solvent into the first reactor containing a catalyst comprising a titanium containing zeolite as catalytically active material;
         (a2') subjecting the feed stream according to (a1) in the first reactor to epoxidation conditions in the presence of the catalyst, obtaining a reaction mixture comprising the propylene oxide and the organic solvent;
         (a3') removing a product stream comprising the propylene oxide and the organic solvent from the first reactor;
      (b') stopping introducing the feed stream into the first reactor;
      (c') washing the catalyst with a liquid aqueous system;
      stage (i') further comprising repeating the sequence of steps (a') to (c') n' times with n' being an integer and being at least 1; the process the preparation of propylene oxide further comprising
   (ii') a stage comprising calcining the catalyst obtained from (c') after having repeated the sequence of steps (a') to (c') n' times;
   wherein the sequence of stages (i') to (ii') is optionally repeated m' times with m' being an integer and being at least 1, wherein in each repetition of the sequence of steps (i') to (ii'), n' is the same or different;
   the process for the preparation of propylene oxide further comprising
   (i") a stage comprising
      (a") continuously preparing propylene oxide in a second reactor comprising
         (a1") introducing a feed stream comprising propene, hydrogen peroxide or a hydrogen peroxide source, and an organic solvent into the second reactor containing a catalyst comprising a titanium containing zeolite as catalytically active material;
         (a2") subjecting the feed stream according to (a1") in the second reactor to epoxidation conditions in the presence of the catalyst, obtaining a reaction mixture comprising the propylene oxide and the organic solvent;
         (a3") removing a product stream comprising the propylene oxide and the organic solvent from the second reactor;
      (b") stopping introducing the feed stream into the second reactor;
      (c") washing the catalyst with a liquid aqueous system;
      stage (i") further comprising repeating the sequence of steps (a") to (c") n" times with n" being an integer and being at least 1; the process the preparation of propylene oxide further comprising
   (ii") a stage comprising calcining the catalyst obtained from (c") after having repeated the sequence of steps (a") to (c") n" times;
   wherein the sequence of stages (i") to (ii") is optionally repeated m" times with m" being an integer and being at least 1, wherein in each repetition of the sequence of steps (i") to (ii"), n" is the same or different;
   wherein during at least one sequence of steps (b') and (c') or at least one sequence of steps (b'), (c') and (ii'), propylene oxide is prepared according to (a").

The present invention is further illustrated by the following Figures, Reference Examples, Examples, and Comparative Examples.

DESCRIPTION OF THE FIGURES

In FIG. 1, the letters and numbers have the following meanings:

A epoxidation unit A
B epoxidation unit B
C distillation unit
D distillation unit
E distillation unit
F part stream distillation unit
G mixer-settler unit
H acetonitrile recovery unit
acetonitrile recycle unit
(1)-(20) streams according to a specifically preferred process as described in the examples
S0, S01, S02, S1, S2, S3, S4, S4b, S5, L1, L2, TL1, TL2, TL2, BL2
    streams according to a preferred process as described in the general description and the examples
In FIG. 2, the letters and numbers have the following meanings:
F1 first fractionation unit of the part stream distillation unit F
F2 second fractionation unit of the part stream distillation unit F
(13), (13a), (14), (15), (15a), (15b), (15c), (16), (19), (20)
    streams according to a specifically preferred process as described in the examples
S1, S2, S3, S4, S4a, S4b, S4c, S5, TL2
    streams according to a preferred process as described in the general description and the examples

EXAMPLES

Reference Example 1: Preparation of a Molding Containing ZnTiMWW Spray Powder

The catalyst in the form of a molding was prepared as described in WO 2013/117536 A2, in Example 5, in particular in Examples 5.1-5.6, on pages 83-99. The methods of characterizing said molding referred to in said Examples 5.1-5.6 are described in Reference Examples 2-10 on pages 66-71 of WO 2013/117536 A2. Characteristic properties of the catalyst are shown in FIGS. 20-27 of WO 2013/117536 A2 and the respective description of said Figures on page 104 of WO 2013/117536 A2.

Reference Example 2: Epoxidation Reaction Setup

Figure 1:
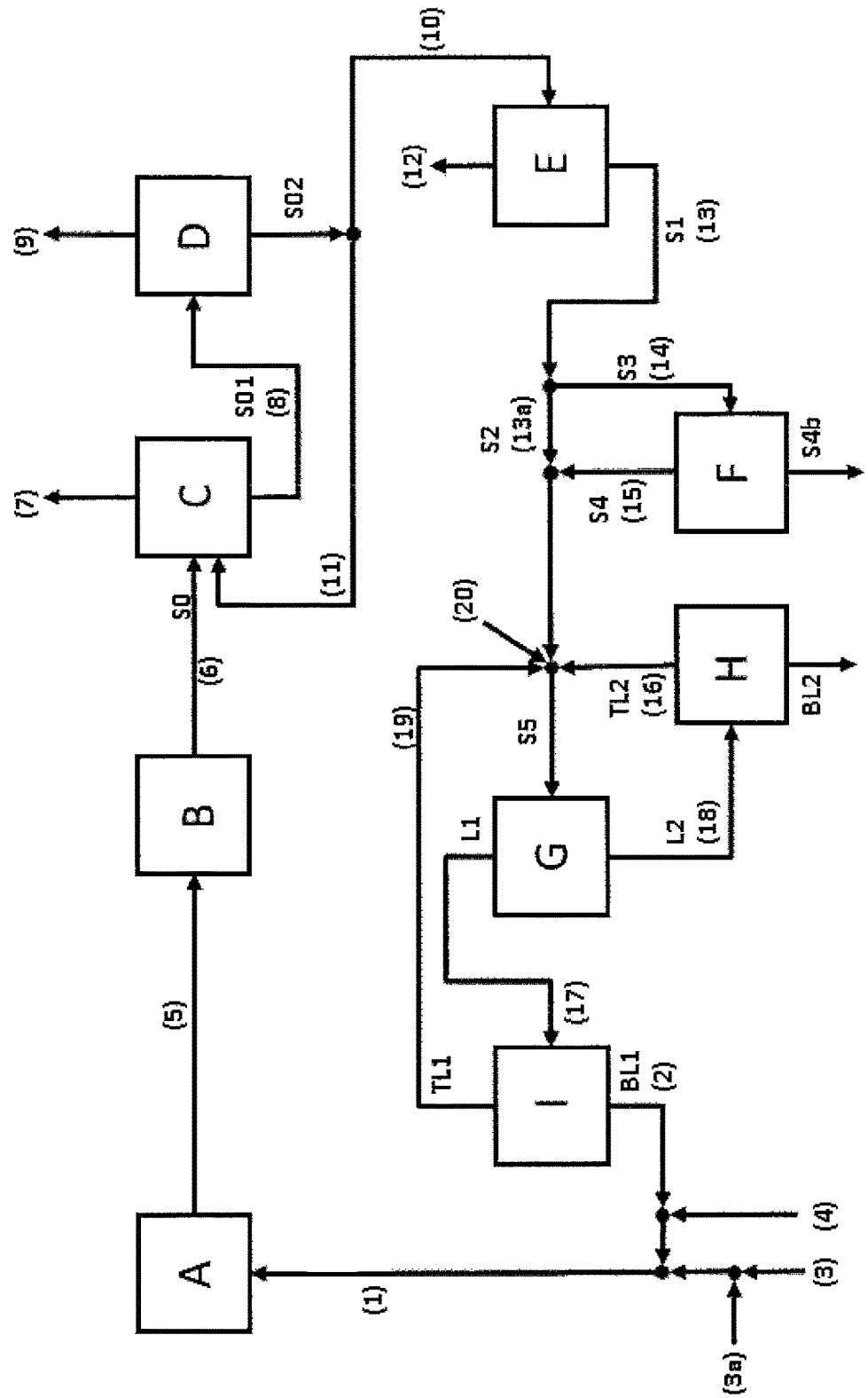
FIG. 1 shows a block diagram of the process according to Reference Example 2.
Figure 2:
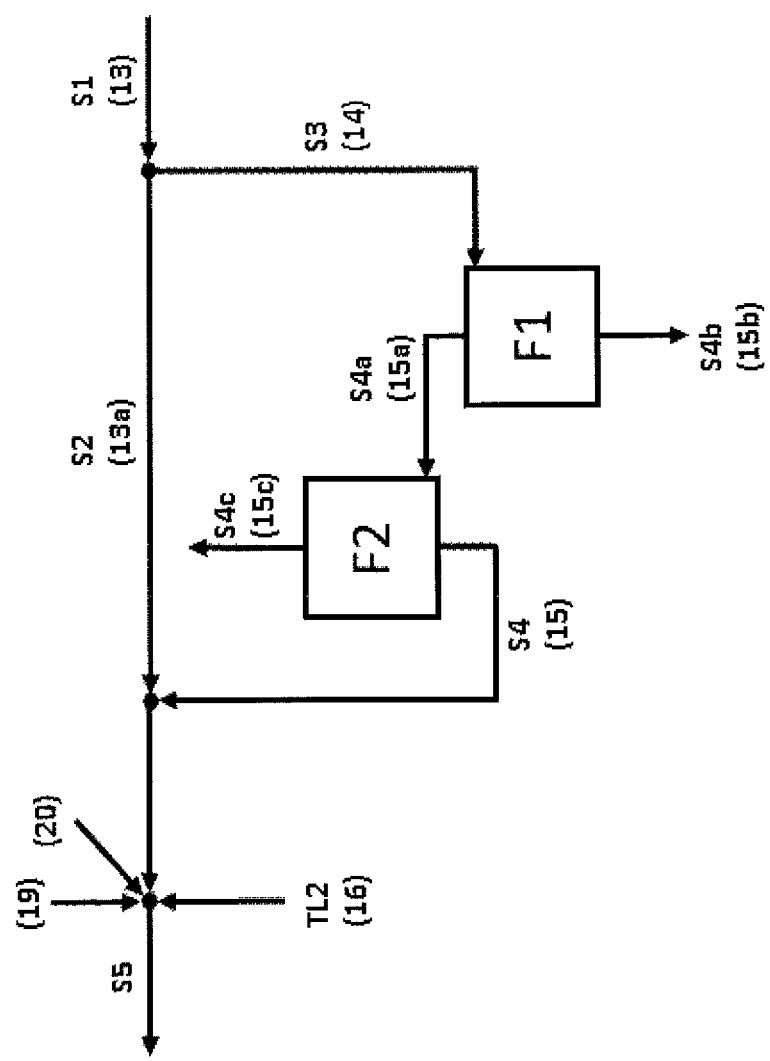
FIG. 2 shows a block diagram the part stream distillation F of FIG. 1 unit in detail.

As to the abbreviations, reference is made to the schemes according to FIGS. 1 and 2, generally described in the section "Description of the Figures". All pressures given are absolute pressures.

1.1 Preparation of Stream S0 (Step (a))
a) Epoxidation in an Epoxidation Main Reactor (Epoxidation Unit A)

The main reactor A was a vertically mounted tube-bundle reactor with 5 tubes (length of the tubes: 12 m, internal tube diameter: 38 mm), each tube being equipped with an axially placed multi-point thermocouple with 10 equally spaced measuring points encased in a suitable thermowell with a diameter of 18 mm. Each tube was charged with 17.5 kg of the ZnTiMWW catalyst moldings as prepared according to Reference Example 1 (post-treated moldings). Free space eventually remaining was filled with steatite spheres (diameter of 3 mm). The heat of reaction was removed by circulating a thermostatized heat transfer medium (water/glycol mixture) on the shell side in co-current to the feed. The flow rate of the heat transfer medium was adjusted so that the temperature difference between entrance and exit did not exceed 1° C. The reaction temperature referred to hereinbelow was defined as the temperature of the heat transfer medium entering the reactor shell. At the reactor exit, the pressure was controlled by a pressure regulator and kept constant at 20 bar.

The reactor was fed from below with a liquid monophasic stream (1). Stream (1) was prepared by mixing four streams (2), (3), (3a) and (4). The temperature of stream (1) was not actively controlled, but was usually in the range from 20 to 40° C.:

Stream (2) having a flow rate of 85 kg/h. At least 99.5 weight-% of stream (2) consisted of acetonitrile, propene and water. This stream (2) came from the bottoms of the acetonitrile recycle distillation unit W.

Stream (3) having a flow rate of 15 kg/h was an aqueous hydrogen peroxide solution having a hydrogen peroxide concentration of 40 weight-% ("crude/washed" grade from Solvay with a TOC in the range of 100 to 400 mg/kg. The aqueous hydrogen peroxide solution was supplied from a storage tank, allowing for a continuous feeding, and fed using a suitable metering pump.

Stream (3a) was an aqueous stream comprising dissolved potassium formate. The further stream was supplied from a storage tank, allowing for a continuous feeding, and was fed using a suitable metering pump. The concentration of the potassium formate was 2.5 weight-%, the feed rate of the stream (S3a) was 370 g/h. Stream (3a) was thoroughly mixed with stream (3) before the combined stream was mixed with the stream resulting from mixing stream (2) and (4).

Stream (4) was a make-up stream of pure acetonitrile (chemical grade, from Ineos, purity about 99.9%, containing between 70-180 weight-ppm propionitrile, 5-20 weight-ppm acetamide and less than 100 weight-ppm water as impurities). Enough fresh acetonitrile was added to compensate for losses in the process. Under regular conditions, an average of from 100 to 150 g/h of make-up acetonitrile were added.

The output stream (5) leaving the epoxidation unit A was sampled every 20 minutes in order to determine the hydrogen peroxide concentration using the titanyl sulfate method and to calculate the hydrogen peroxide conversion. The hydrogen peroxide conversion was defined as $100 \times (1 - m_{out}/m_{in})$ wherein $m_{in}$ is the molar flow rate of $H_2O_2$ in the reactor and $m_{out}$ is the molar flow rate of $H_2O_2$ in the reactor outlet. Based on the respectively obtained hydrogen peroxide conversion values, the inlet temperature of the heat transfer medium was adjusted in order to keep the hydrogen peroxide conversion essentially constant in the range of from 90 to 92%. The inlet temperature of the heat transfer medium was set at 30° C. at the start of a given run with a fresh batch of the epoxidation catalyst and was increased, if necessary, to maintain the hydrogen peroxide conversion in the mentioned range. The required temperature increase was usually less than 1 K/d.

The output stream (5) leaving the epoxidation unit A was passed through a heat exchanging unit. The stream leaving the heat exchanging unit (stream (6), S0) was fed to Epoxidation Unit B.

b) Epoxidation in a Finishing Reactor (Epoxidation Unit B)

The finishing reactor B was a fixed bed reactor operated adiabatically. In this context, the term "adiabatic" refers to an operation mode according to which no active cooling is carried out and according to which the finishing reactor is suitably insulated in order to minimize heat losses). The finishing reactor B had a length of 4 m and a diameter of 100 mm. The reactor was filled with 9 kg of the same epoxidation catalyst which was used in the main epoxidation reactor A. Spare space was filled with steatite spheres (diameter of 3 mm). The operating pressure of the finishing reactor B was 10 bar which was kept constant by a suitable pressure regulator at the reactor exit. The output of the finishing reactor B was sampled every 20 min in order to determine the hydrogen peroxide concentration using the titanyl sulfate method.

The effluent of the finishing reactor B, stream (6), was depressurized into a flash drum, and both the liquid and the gas from this drum were fed to a light boiler separation column (distillation unit C).

Stream (6) (stream S0) had in average an acetonitrile content of from 69 to 70 weight-%, a propylene oxide content of from 9-11 weight-% such as 9.8 weight-%, a water content of 17 weight-%, a propene content of about 3 weight-%, a propane content of about 0.05 weight-%, a hydrogen peroxide content of about 250 weight-ppm, a propene glycol content of about 0.1 weight-% and an oxygen content of about 150 weight-ppm.

1.2 Separation of Propylene Oxide from Stream S0 to Obtain Stream S1 (Step (b))

a) Separation of Light Boilers from Stream (6) (Stream S0) to Obtain a Stream (8) (Stream S01)

Stream (6) was sent to a light boiler separation column (distillation unit C) operated at 1.1 bar. The distillation column had a length of 8.5 m, a diameter of 170 mm, and was equipped with 40 bubble trays, an evaporator at the bottom and a condenser at the top. The column was operated as a mixed washing/distillation tower. As a washing agent, part of the bottoms stream of distillation unit D (stream 11, about 20-30 kg/h) was taken off, cooled to 10° C. and introduced at the top of the column. Liquid and gaseous inlet streams were introduced the column at different points. The feed point of the liquid portion of stream (6) was above bubble tray 37; the gaseous portion of stream (6) was introduced into the column above bubble tray 28 (counted from the top). The gaseous stream (7) leaving the cooling means at the top of the column contained mainly propene, propane (which was contained as impurity in the polymer-grade propene used), oxygen formed as a by-product and small amounts of other light boilers (acetonitrile (1-2 volume-%), propionaldehyde (about 200 volume-ppm), acetone (about 100 volume-ppm, $H_2$ (about 400 volume-ppm), $CO_2$ (about 400 volume-ppm) and acetaldehyde (about 100 volume-ppm)), and was essentially free of propylene oxide (less than 300 volume-ppm). This top stream was sent to the flare for disposal. The bottom stream of the light boiler separation column (stream (8), that is stream S01) having a temperature of 70° C., had a propene content of from 100 to 200 weight-ppm.

b) Separation of Propylene Oxide from Stream (8) (Stream S01) to Obtain a Stream S02

The stream S01 obtained according to section 1.2 a) above was introduced into a distillation column (distillation unit D) in order to separate propylene oxide from the stream S01. The column had a height of 50 m and a diameter of 220 mm and was equipped with a packing (Sulzer BX64) with a total packing length of 27.5 m divided into 8 beds with a length of 3060 mm each and two beds with a length of 1530 mm each. Between each bed intermediate flow distributors were installed. The column was operated at a top pressure of 750 mbar. The feed point of stream S01 was located below the fourth packing bed, counted from the top. The overhead stream of the column was condensed and partly returned to the column as reflux (reflux ratio approximately 5:1). The remainder (stream (9)), having a flow rate of 10.1 kg/h, was taken as overhead product and essentially consisted of propylene oxide having a purity of more than 99.9 weight-%. The bottoms evaporator was operated in such a way that the propylene oxide concentration in the bottoms stream was below 100 weight-ppm. The resulting temperature of the bottoms stream was about 69° C. The stream S02 was then divided in two. The major portion of it (stream (10)), with a flow rate of ca. 85 kg/h was sent to the next distillation column (distillation unit E). The remainder (stream (11), 20-30 kg/h) was cooled and recirculated to the top of the light boiler separation column (distillation unit C) as washing agent as described above in section 1.2 a). This stream S02 had an acetonitrile content of about 80 weight-%, a propylene oxide content of less than 100 wt.-ppm, a water content of about 20 weight-%, a propene glycol content of about 0.1 weight-% and a hydroxypropanol content of about 0.1 weight-%.

c) Separation of Light Boiling Compounds from Stream (10) (Stream S02) to Obtain a Stream (13) (Stream S1)

The stream S02 obtained according to section 1.2 b) above was introduced into a lights separation column (distillation unit F). This lights separation column had a height of 8 m and a nominal diameter of 150 mm and was equipped with 35 bubble trays. The column was operated at a top pressure of 2 bar, and the stream S02 was introduced above bubble tray number 7 (counted from the bottom). The overhead stream obtained (stream (12), flow rate about 1 kg/h) left the column with a temperature of from 40 to 45° C. and was not condensed as the column was operated with no internal reflux stream. Besides acetonitrile (6500 vol.-ppm), this overhead stream contained mainly nitrogen which was employed to keep the column operating pressure at a value of 2 bar) and small amounts of light boilers (acetaldehyde (900 vol.-ppm), oxygen (300 vol.-ppm), and propionaldehyde (320 vol.-ppm). This top stream was sent to the flare for disposal. The sump evaporator was operated by feeding it with a constant amount (5 kg/h) of saturated steam at a pressure of 16 bar. The bottom temperature of the column was 100° C. The bottoms stream, stream S1, mainly consisted of acetonitrile and water, the remainder being high boilers. This stream S1 had an acetonitrile content of about 80 weight-% and a water content of about 20 weight-%.

1.3 Dividing Stream S1 into Streams S2 and S3 (Step (C))

Step (c), the stream S1, flow rate 86 kg/h, obtained according to section 1.2 c) above, was divided into two streams, streams S2 (stream (13a according to FIG. 1) and S3 (stream 14 according to FIG. 1). Stream S2 had a flow rate of 84 kg/h and stream S3 had a flow rate of 2 kg/h. Stream S3, 2.3% of stream S1, was subjected to part stream distillation unit F (part stream distillation columns).

1.4 Part-Stream Distillation of Stream S1 (Step (d))

The first fractionation unit, i.e. the first distillation column, F1, had a height of 9.5 m and a diameter of 85 mm and was equipped with 6.5 meters of metal structured Rombopak 9M packing installed in three identical beds. Above the first bed of the structured packing counted from the top, the stream S3 ((stream 14)) was introduced in the first distillation column. The temperature of the stream S3 stream was 60±3° C. The first distillation column was operated at a top pressure of about 1.4 bar and a bottoms temperature of 92±5° C. No reflux was applied. The amount of steam fed to the bottoms evaporator of the first fractionation unit was controlled in such a way that the concentration of acetonitrile in the bottoms was in the range of from 10 to 25 weight-%. The bottoms stream S4b (stream (15b), about 3% of the stream S3) was removed. This stream consisted mainly of water (72-85 weight-%) and acetonitrile (10-24 weight-%). The sum of all the analyzed high-boiling components (27 components) varied in the range of 2-10 weight-%. The top stream, vapor fraction stream S4a (stream 15a), having a temperature of from 85±3° C., was not condensed and passed to the bottom of the second fractionation unit, i.e. the second distillation column, F2. S4a entered F2 below the last bed of the structured packing counted from the top. F2 had a height of 9.5 m and a diameter of 85 mm and was equipped with 6.5 m of metal structured Rombopak 9M packing installed in 3 identical beds. The second distillation column was operated at a top pressure of about 1.25 bar and a bottoms temperature of 85±5° C. The top stream, vapor fraction stream S4c (stream 15c), at most 1% of the stream S4a), was fully condensed by an external overhead condenser (not shown in FIG. 2) and applied essentially completely to use the condensed, liquid stream as reflux to the second distillation column. The liquid bottoms stream S4 (stream 15), was removed and passed to the next step (recycling of the stream 54). The stream S4 had an acetonitrile content of about 80 weight-% and a water content of about 20 weight-%.

1.5 Recycling of the Stream S4 (Step (4))

a) Preparing a Liquid Stream S5

The stream S4, (stream 15 according to FIG. 1 and FIG. 2) was admixed with stream S2 (stream 13a) according to FIG. 1 and FIG. 2). Thus, the stream S4 was pumped back into the bulk process acetonitrile solvent stream. Mixing took place at a point downstream of where stream S3 was diverted from stream S1. This combined stream having a flow rate of 86 kg/h was mixed with a liquid stream P (referred to as stream (20) in FIG. 1 and FIG. 2) to obtain a stream S5. Stream P was fresh propene stream containing propane (polymer grade, purity >96 weight-%, liquefied under pressure, feed rate: 10.9 kg/h). In order to obtain the stream S5, the combined stream of S2 and S4 was further mixed with two other streams: the first one of these streams is stream (16) according to FIG. 1, said stream being obtained from the top of the distillation unit H. The second one of these streams is stream (19) according to FIG. 1, said stream being obtained from the acetonitrile recovery unit I. Both streams (16) and (19) are described in detail hereinunder.

b) Adjusting the temperature of stream S5 and separating liquid phases L1 and L2

The stream S5 having a flow rate of 130 kg/h±10 kg/h was then fed to a mixer-settler unit operated at 18 bar and a temperature in the range of 15±5° C. The settler tank had a volume of 5.3 liters. Two liquid phases L1 and L2 were obtained, an aqueous phase L2 and an organic phase L1. The upper organic phase L1 was removed from the settler tank as stream (17), the lower aqueous phase L2 was removed from the settler tank as stream (18). The stream (17) had a flow rate in the range of 110 kg/h±11 kg/h. The stream (17) then was passed to the acetonitrile recycle unit I, the stream (18) was passed to the acetonitrile recovery unit H from which the stream (16) mentioned above was obtained. The stream (17) thus obtained had an acetonitrile content of about 45-51 weight-%, a propene content of about 49-55 weight-% and a water content of about 2 to 5 weight-%. The stream (18) thus obtained had an acetonitrile content of about 19-21 weight-%, a water content of about 79-81 weight-% and a propene content of less than 0.5 weight-%.

c) Acetonitrile Recovery (Acetonitrile Recovery Unit H)

In order to recycle as much solvent as possible, and in order to minimize acetonitrile losses, the stream (18) was introduced into a distillation column from which the stream (16), also referred to as stream TL2, was obtained as top stream which in turn was recycled into the solvent stream as described above. For this purpose, a distillation column with a height of 9.5 m and a diameter of 100 mm, equipped with 50 bubble trays was used. The column was operated at a top pressure of 1.5 bar with a reflux ratio of 1:4. Stream (18) was fed to the column above bubble tray 26 (counted from the bottom). The bottoms temperature was about 113° C., and the bottoms product consists mainly of water containing high boiling by-products. A typical composition of the bottoms stream was as follows (weight-% given in parenthesis): water (>99.0), propene glycol (0.5), acetonitrile (at most 0.001), dipropylene glycol (0.06), acetamide (0.01), acetic acid (0.03), TOC (2.4)). After optional metering and analyzing, this stream was discarded. The overhead product (stream (16)=stream TL2) had the following typical composition ranges (weight-% given in parenthesis): acetonitrile (75-80), water (15-20), low boilers (e.g. propene, 1). As described above stream (16) is recycled to the feed stream which is passed to the mixer-settler unit.

d) Acetonitrile Recycling (Acetonitrile Recycling Unit I)

For acetonitrile recycle, the stream (17) obtained from the mixer-settler unit G was introduced into a distillation column with a height of 10 m and a nominal diameter of 200 mm, equipped with 40 bubble trays. The column was operated at a top pressure of 18 bar with a reflux ratio of 1:4. Stream (17) was fed to the column above bubble tray 26 (counted from the top). The top product (stream (19)), also referred to as stream TL1, containing mainly propene (ca. 97 vol.-%) with small amounts of propane (ca. 1-3 vol.-%) was returned to the feed of the mixer-settler unit G as described above. Thus, excess propene was removed from steam (17) and recycled. The bottoms stream (stream (2), also referred to as stream BL1), had a temperature in the range of from 106 to 110° C. The precise operation parameters of the column, like energy input in the sump, are adjusted in such a way that the amount of propene returned to the reactor with stream (2) is in a range such that the molar ratio of propene to hydrogen peroxide in stream (1) was about 1:1.43. For the above mentioned feed rate of 15 kg/h of aqueous hydrogen peroxide, this means that the conditions needed to be adjusted such that the flow rate of propene in stream (2) was about 9.7 kg/h. Prior to feeding stream (2) to the main epoxidation reactor A, acetonitrile (stream (4), chemical grade, from Ineos, purity about 99.9%, containing between 70-180 weight-ppm propionitrile, 5-20 weight-ppm acetamide and <100 weight-ppm water as impurities) was optionally added to compensate for possible solvent losses.

The exact amount of additionally added acetonitrile required depended on the losses in exit streams and in by-products but also on the number of samples taken for analytics. A typical amount of additionally added acetonitrile for the above-described process design may be in the range of from 100 to 150 g/h.

Example 1: One-Time ZnTiMWW Catalyst Regeneration

The partial ZnTiMWW catalyst regeneration was performed based on the epoxidation reaction setup as described in Reference Example 2 above. The reactor was loaded with the ZnTiMWW catalyst according to Reference Example 1. The epoxidation reaction was continuously operated until the selectivity regarding the formation of propylene oxide in (a2) based on hydrogen peroxide decreased by 2% relative to the average selectivity regarding the formation of propylene oxide in (a2) based on hydrogen peroxide during the first 1000 h of carrying out step (a). Then the reaction was stopped and the reactor flushed free of $H_2O_2$, propylene and propylene oxide. After decompression and emptying, the reactor was flushed at 70° C. with demineralized water from top to bottom with a LHSV of about 7 m/h (the LHSV being based on the cross section of the empty tubes) for at least 3 hours. After this time, the liquid aqueous system leaving the reactor showed a total organic carbon concentration of less than 0.1% of the maximum value detected and the total volume of the liquid aqueous system obtained from the reactor in washing process was larger than the volume of the reactor. Then, the reactor was emptied and restarted. Continuous operation according to Reference Example 2 was resumed and carried out for approximately 1500 h until the reaction temperature reached again the value it had before the regeneration.

Comparative Example 1: Continuous Operation According to Reference Example 2 without Regeneration As a comparative Example, the process according to Reference Example 2 was carried out for 2,500 h without regenerating the catalyst.

Results from Example 1 and Comparative Example 1

The results from example 1 and comparative example 1 are discussed hereinafter and shown in Table 1. The inlet temperature of the heat transfer medium of epoxidation unit A both in Example 1 and Comparative Example 1 was adjusted during the continuous operation according to Reference Example 2 in order to keep the hydrogen peroxide conversion essentially constant in the range of from 90 to 92% (cf. Reference Example 2, section 1.1 a). The resulting temperature of the heat transfer medium (cooling water) of epoxidation unit A after a total operation time of 2,500 h is shown in the table 1 both for Comparative Example 1 and for Example 1. Further, the deactivation rate is given as the ratio of the difference of the temperature of the heat transfer medium at the inlet at the end of the experiment and the beginning of the experiment divided by the total operation time of 2,500 h, expressed in ° C./day. Yet further, the selectivity S of the epoxidation reaction based on hydrogen peroxide after the total operation time of 2,500 h is provided in Table 1. The selectivity $S/\%=(n(PO)/n(H_2O_2))\times 100$ wherein n(PO) is the molar amount of propylene oxide detected directly downstream to unit B and $n(H_2O_2)$ is the molar amount of hydrogen peroxide converted in the epoxidation reaction.

TABLE 1

|  | Comparative Example 1 | Example 1 |
| --- | --- | --- |
| Temperature of the cooling water of epoxidation unit A after 2,500 h time on stream/° C. | 55 | 49 |
| Deactivation rate (delta(T)/delta(t))/° C./day | 0.240 | 0.182 |
| Selectivity S/% | 96.5 | 97.2 |

As clearly shown in Table 1, the process according to the present invention allows to run the epoxidation unit A after a total operation time of 2,500 h at a significantly lower temperature of the cooling water, i.e. the catalyst exhibits a significantly better performance than in comparative example 1. Further, also the deactivation rate (delta(T)/delta (t)) differs for the two experiments and is significantly lower with regard to the inventive example. Yet further, the process according to the present invention provides, after a total operation time of 2,500 h, a significantly higher selectivity than the comparative example 1.

The regenerated catalyst of example 1 exhibited a differential conversion temperature of 1 K, wherein the differential conversion temperature is defined as the absolute difference between (A1) the temperature at which the conversion of the hydrogen peroxide 90-92% was achieved when the regenerated catalyst is used as catalyst, and (B1) the temperature at which said determined conversion of the hydrogen peroxide was achieved when the respective fresh catalyst was used under otherwise identical epoxidation reaction conditions. Further, the regenerated catalyst of example 1 exhibited a differential selectivity of 0.3% points wherein the differential selectivity is defined as the absolute difference in % points between (A2) the selectivity based on the hydrogen peroxide in the epoxidation process in which the regenerated catalyst is used as catalyst, and (B2) the selectivity based on the hydrogen peroxide in said epoxidation process in which the respective fresh catalyst is used as catalyst under otherwise identical epoxidation reaction conditions.

Example 2.1: ZnTiMWW Catalyst Regeneration According to the Invention Including Three Washing Steps The partial ZnTiMWW catalyst regeneration was performed based on the epoxidation reaction setup as described in Reference Example 2 above.

Epoxidation

The partial ZnTiMWW catalyst regeneration was performed based on the epoxidation reaction setup as described in Reference Example 2 above. The main reactor was loaded with the ZnTiMWW catalyst according to Reference Example 1. The epoxidation reaction was continuously operated for approximately 1300 hours until the "epoxidation reaction temperature", defined as the temperature of the heat transfer medium at the entrance of the jacket of the main reactor whose staffing value at the beginning of the epoxidation reaction was 30° C., had reached a value of 50° C. At that point in time, the epoxidation reaction was stopped by stopping the flow of hydrogen peroxide; the acetonitrile and propene flows were continued until the epoxidation in the tubes was completed. Then, the reactor was flushed free of $H_2O_2$, propylene and propylene oxide by passing a mixture of acetonitrile and water through the reactor (80 weight-% acetonitrile, 20 weight-% water) wherein the temperature of this mixture was 50° C., followed by draining the major portion of the mixture of acetonitrile and water from the reactor.

First Washing Step

Subsequently, the reaction tubes were filled from below with water having a temperature of 70° C., and water having a temperature of 70° C. was then passed from the top downward through the tubes for about 6 h. The water wash was stopped once the conductivity of the outflowing water was below 200 microSiemens. The water was then drained from the reactor.

Epoxidation

Continuous operation according to Reference Example 2 was resumed and carried out for approximately 1400 h until the reaction temperature reached again the value of 50° C. At that point in time, the epoxidation reaction was stopped by stopping the flow of hydrogen peroxide; the acetonitrile and propene flows were continued until the epoxidation in the tubes was completed. Then, the reactor was flushed free of $H_2O_2$, propylene and propylene oxide by passing a mixture of acetonitrile and water through the reactor (80 weight-% acetonitrile, 20 weight-% water) wherein the temperature of this mixture was 50° C., followed by draining the major portion of the mixture of acetonitrile and water from the reactor.

Second Washing Step

Subsequently, the reaction tubes were filled from below with water having a temperature of 70° C., and water having a temperature of 70° C. was then passed from the top downward through the tubes for about 6 h. The water wash was stopped once the conductivity of the outflowing water was below 200 microSiemens. The water was then drained from the reactor.

Epoxidation

Continuous operation according to Reference Example 2 was resumed and carried out for approximately 1200 h until the reaction temperature reached again the value of 50° C. At that point in time, the epoxidation reaction was stopped by stopping the flow of hydrogen peroxide; the acetonitrile and propene flows were continued until the epoxidation in the tubes was completed. Then, the reactor was flushed free of $H_2O_2$, propylene and propylene oxide by passing a mixture of acetonitrile and water through the reactor (80 weight-% acetonitrile, 20 weight-% water) wherein the temperature of this mixture was 50° C., followed by draining the major portion of the mixture of acetonitrile and water from the reactor.

Residual amounts of acetonitrile and water were removed from the reactor by passing nitrogen through the catalyst bed at a temperature of the nitrogen of 70° C.

Third Washing Step

Subsequently, the reaction tubes were filled from below with water having a temperature of 70° C., and water having a temperature of 70° C. was then passed from the top downward through the tubes for about 6 h. The water wash was stopped once the conductivity of the outflowing water was below 200 microSiemens. The water was then drained from the reactor.

Calcining Step

Then, nitrogen was passed through the catalyst bed for approximately 60 hours at an initial temperature of the nitrogen of 70° C. wherein this temperature was ramped to a value of 100° C. at 10 K/h. Subsequently, the catalyst was calcined by passing a gas mixture of air and nitrogen through the catalyst bed at a flow rate of 0.58 kg/s. The temperature of said mixture was further continuously ramped at 10 K/h from its initial value of 100° C. to a final value of 450° C. and then kept essentially constant at a value of 450° C. for 6 hours. At the beginning of the calcination, the gas mixture passed into the reactor had an oxygen content of 4 volume-%. Once having reached 450° C., said oxygen content was adjusted to a value of 21 volume-%. After the calcination at 450° C., the reactor was cooled to a temperature of approximately 30° C.

Epoxidation

Continuous operation according to Reference Example 2 was resumed and carried out for approximately 1000 h.

Example 2.2: ZnTiMWW Catalyst Regeneration According to the Invention Including Two Washing Steps The partial ZnTiMWW catalyst regeneration was performed based on the epoxidation reaction setup as described in Reference Example 2 above.

Epoxidation

The main reactor was loaded with the ZnTiMWW catalyst according to Reference Example 1. The epoxidation reaction was continuously operated for approximately 1200 hours until the "epoxidation reaction temperature", defined as the temperature of the heat transfer medium at the entrance of the jacket of the main reactor whose starting value at the beginning of the epoxidation reaction was 30° C., had reached a value of 50° C. At that point in time, the epoxidation reaction was stopped by stopping the flow of hydrogen peroxide; the acetonitrile and propene flows were continued until the epoxidation in the tubes was completed. Then, the reactor was flushed free of $H_2O_2$, propylene and propylene oxide by passing a mixture of acetonitrile and water through the reactor (80 weight-% acetonitrile, 20 weight-% water) wherein the temperature of this mixture was 50° C., followed by draining the major portion of the mixture of acetonitrile and water from the reactor.

First Washing Step

Subsequently, the reaction tubes were filled from below with water having a temperature of 70° C., and water having a temperature of 70° C. was then passed from the top downward through the tubes for about 6 h. The water wash was stopped once the conductivity of the outflowing water was below 200 microSiemens. The water was then drained from the reactor.

Epoxidation

Continuous operation according to Reference Example 2 was resumed and carried out for approximately 1300 h until the reaction temperature reached again the value of 50° C. At that point in time, the epoxidation reaction was stopped by stopping the flow of hydrogen peroxide; the acetonitrile and propene flows were continued until the epoxidation in the tubes was completed. Then, the reactor was flushed free of 1-1202, propylene and propylene oxide by passing a mixture of acetonitrile and water through the reactor (80 weight-% acetonitrile, 20 weight-% water) wherein the temperature of this mixture was 50° C., followed by draining the major portion of the mixture of acetonitrile and water from the reactor.

Residual amounts of acetonitrile and water were removed from the reactor by passing nitrogen through the catalyst bed at a temperature of the nitrogen of 70° C.

Second Washing Step

Subsequently, the reaction tubes were filled from below with water having a temperature of 70° C., and water having a temperature of 70° C. was then passed from the top downward through the tubes for about 6 h. The water wash was stopped once the conductivity of the outflowing water was below 200 microSiemens. The water was then drained from the reactor.

Calcining Step

Then, nitrogen was passed through the catalyst bed for approximately 60 hours at an initial temperature of the nitrogen of 70° C. wherein this temperature was ramped to a value of 100° C. at 10 K/h. Subsequently, the catalyst was calcined by passing a gas mixture of air and nitrogen through the catalyst bed at a flow rate of 0.58 kg/s. The temperature of said mixture was further continuously ramped at 10 K/h from its initial value of 100° C. to a final value of 450° C. and then kept essentially constant at a value of 450° C. for 6 hours. At the beginning of the calcination, the gas mixture passed into the reactor had an oxygen content of 4 volume-%. Once having reached 450° C., said oxygen content was adjusted to a value of 21 volume-%. After the calcination at 450° C., the reactor was cooled to a temperature of approximately 30° C.

Epoxidation

Continuous operation according to Reference Example 2 was resumed and carried out for approximately 1000 h.

Comparative Example 2: ZnTiMWW Catalyst Regeneration Including One Washing Step

Epoxidation

The ZnTiMWW catalyst regeneration was performed based on the epoxidation reaction setup as described in Reference Example 2 above. The main reactor was loaded with the ZnTiMWW catalyst according to Reference Example 1. The epoxidation reaction was continuously operated for approximately 2200 hours until the "epoxidation reaction temperature", defined as the temperature of the heat transfer medium at the entrance of the jacket of the main reactor whose starting value at the beginning of the epoxidation reaction was 30° C., had reached a value of 50° C. At that point in time, the epoxidation reaction was stopped by stopping the flow of hydrogen peroxide; the acetonitrile and propene flows were continued until the epoxidation in the tubes was completed. Then, the reactor was flushed free of $H_2O_2$, propylene and propylene oxide by passing a mixture of acetonitrile and water through the reactor (80 weight-% acetonitrile, 20 weight-% water) wherein the temperature of this mixture was 50° C., followed by draining the major portion of the mixture of acetonitrile and water from the reactor.

Residual amounts of acetonitrile and water were removed from the reactor by passing nitrogen through the catalyst bed at a temperature of the nitrogen of 70° C.

Washing Step

Subsequently, the reaction tubes were filled from below with water having a temperature of 70° C., and water having a temperature of 70° C. was then passed from the top downward through the tubes for about 6 h. The water wash was stopped once the conductivity of the outflowing water was below 200 microSiemens. The water was then drained from the reactor.

Calcining Step

Then, nitrogen was passed through the catalyst bed for approximately 60 hours at an initial temperature of the nitrogen of 70° C. wherein this temperature was ramped to a value of 100° C. at 10 K/h. Subsequently, the catalyst was calcined by passing a gas mixture of air and nitrogen through the catalyst bed at a flow rate of 0.58 kg/s. The temperature of said mixture was further continuously ramped at 10 K/h from its initial value of 100° C. to a final value of 450° C. and then kept essentially constant at a value of 450° C. for 6 hours. At the beginning of the calcination, the gas mixture passed into the reactor had an oxygen content of 4 volume-%. Once having reached 450° C., said oxygen content was adjusted to a value of 21 volume-%. After the calcination at 450° C., the reactor was cooled to a temperature of approximately 30° C.

Epoxidation

Continuous operation according to Reference Example 2 was resumed and carried out for approximately 1000 h.

Results from Examples 2.1 and 2.2 and Comparative Example 2

The results from examples 2.1 and 2.2 and comparative example 2 are discussed hereinafter and shown in Table 2 below. The inlet temperature of the heat transfer medium of epoxidation unit A both in Examples 2.1 and 2.2 and Comparative Example 2 was adjusted during the continuous operation according to Reference Example 2 in order to keep the hydrogen peroxide conversion essentially constant at approximately 96%. The selectivity S of the epoxidation reaction based on hydrogen peroxide as provided in Table 2 is defined as $(n(PO)/n(H_2O_2))\times 100$ wherein n(PO) is the molar amount of propylene oxide detected directly downstream to unit B and $n(H_2O_2)$ is the molar amount of hydrogen peroxide converted in the epoxidation reaction.

TABLE 2

| | Example 2.1 | Example 2.2 | Comparative Example 2 |
|---|---|---|---|
| Epoxidation time before first washing step/h | 1300 | 1200 | 2200 |
| Epoxidation time after the first until the second washing step/h | 1400 | 1300 | — |
| Epoxidation time after the second until the third washing step/h | 1200 | — | — |
| Total epoxidation time until calcination/h | 3900 | 2500 | 2200 |
| Selectivity immediately before calcination/% | 97.2 | 97.1 | 96.8 |
| Selectivity 1000 hours after calcination/% | 97.3 | 97.4 | 97.2 |

As clearly shown in Table 2, a process according to the invention wherein one washing step (example 2.2) and two washing steps (example 2.1) is/are carried out without a subsequent calcination step lead to a slight, but nevertheless existing improve in selectivity (1000 hours after calcination) compared to a common process (comparative example 2) according to which a calcination is carried out directly after the (only) washing step. This remarkable result is achieved although the total epoxidation time until the calcination step is higher (plus 300 hours with regard to example 2.2) or even significantly higher (plus 1700 hours with regard to example 2.1). Thus, it is convincingly shown that the inventive concept of a partial regeneration according to stage (i) which avoids a calcination step after each washing step and, thus, represents a significantly less complex process, unexpectedly leads to even improved results with regard to the most important parameter of—in particular—an industrial-scale process, i.e. the selectivity with regard to the valuable product.

CITED LITERATURE

WO 98/55229 A1
EP 1 221 442 A1
WO 2005/000827 A1
WO 2007/013739 A1
Ullmann's Encyclopedia of Industrial Chemistry, 5th edition, volume 13, pp. 447-456
Atlas of Zeolite Framework Types, 5th edition, Elsevier, London, England (2001)
US 2007043226 A1
U.S. Pat. No. 6,114,551
Wu et al., "Hydrothermal Synthesis of a novel Titanosilicate with MWW Topology", Chemistry Letters (2000), pp. 774-775
WO 2013/117536 A2

The invention claimed is:
1. A process for regenerating a catalyst comprising a titanium comprising zeolite of MWW framework structure as catalytically active material, the process comprising:

(i) a stage comprising
(a) continuously preparing propylene oxide by a process comprising, in the following order:
(a1) introducing a feed stream comprising propene, hydrogen peroxide or a hydrogen peroxide source, and an organic solvent into a reactor comprising a catalyst comprising the titanium comprising zeolite of MWW framework structure as catalytically active material;
(a2) subjecting the feed stream according to (a1) in the reactor to epoxidation conditions in the presence of the catalyst, obtaining a reaction mixture comprising the propylene oxide and the organic solvent; and
(a3) removing a product stream comprising the propylene oxide and the organic solvent from the reactor;
(b) stopping introducing the feed stream into the reactor;
(c) washing the catalyst with a liquid aqueous system comprising at least 50 weight-% water, based on the total weight of the liquid aqueous system; and then,
(ii) a stage comprising calcining the catalyst obtained from (c), wherein the calcining is performed at a temperature of the catalyst in the range of from 300° C. to 600° C. using a gas stream comprising oxygen;
wherein the sequence of steps (a) to (c) in stage (i) is performed n times, where n is an integer and at least 2, such that the washing of the catalyst with a liquid aqueous system according to step (c) is followed by the continuous preparation of propylene according to step (a) at least once without an intervening calcination stage (ii).

2. The process of claim 1, wherein the organic solvent is methanol or acetonitrile.

3. The process of claim 1, wherein at least 99 weight-% of the framework structure of the titanium comprising zeolite of MWW framework structure consists of silicon, titanium, and oxygen.

4. The process of claim 1, wherein the titanium comprising zeolite of MWW framework structure comprises Zn.

5. The process of claim 1, wherein the catalyst comprising a titanium comprising zeolite of MWW framework structure is present in the reactor as fixed-bed catalyst.

6. The process of claim 1, wherein the liquid aqueous system according to (c) comprises at least 95 weight-% water, based on the total weight of the liquid aqueous system.

7. The process of claim 1, wherein according to (c), the washing of the catalyst is carried out in the reactor comprising the catalyst in continuous mode.

8. The process of claim 7, wherein the reactor according to (a) is a tube reactor or a tube bundle reactor and the washing according to (c) is performed with the liquid aqueous system at a liquid hourly space velocity (LHSV) in the range of from 1 to 20 m/h.

9. The process of claim 1, wherein the washing according to (c) is performed at a temperature of the liquid aqueous system in the range of from 30 to 90° C.

10. The process of claim 1, wherein the washing according to (c) is performed until the total organic carbon concentration of the liquid aqueous system after having been contacted with the catalyst is at most 5% of the maximum total organic carbon concentration detected during the washing in (c).

11. The process of claim 1, wherein the sequence of steps (b) and (c) is carried out when the selectivity of the epoxidation reaction according to (a2) has decreased by 4% or less, relative to the average selectivity of the epoxidation reaction according to (a2) during the first 100 h of carrying out step (a), wherein the selectivity of the epoxidation reaction is defined as the molar amount of propylene oxide obtained in (a2) relative to the molar amount of hydrogen peroxide converted in (a2).

12. The process of claim 1, wherein n is in the range of from 2 to 7.

13. The process of claim 1, wherein the calcining according to stage (ii) is performed at a temperature of the catalyst in the range of from 350 to 550° C.

14. The process of claim 1, wherein the calcining according to stage (ii) is carried out in the reactor comprising the catalyst.

15. The process of claim 1, further comprising:
repeating stages (i) and (ii) m times, wherein m is an integer and at least 1, and wherein in each repetition of stages (i) and (ii) the integer n is the same or different.

16. The process of claim 15, wherein m is an integer from 1 to 6.

17. A continuous process for preparing propylene oxide, the process comprising:
(i') a stage comprising
(a') continuously preparing propylene oxide in a first reactor by a process comprising, in the following order:
(a1') introducing a feed stream comprising propene, hydrogen peroxide or a hydrogen peroxide source, and an organic solvent into the first reactor comprising a catalyst comprising a titanium comprising zeolite of MWW framework structure as catalytically active material;
(a2') subjecting the feed stream according to (a1') in the first reactor to epoxidation conditions in the presence of the catalyst, obtaining a reaction mixture comprising the propylene oxide and the organic solvent; and
(a3') removing a product stream comprising the propylene oxide and the organic solvent from the first reactor;
(b') stopping introducing the feed stream into the first reactor;
(c') washing the catalyst with a liquid aqueous system comprising at least 50 weight-% water, based on the total weight of the liquid aqueous system; and then
(ii') a stage comprising calcining the catalyst obtained from (c'), wherein the calcining is performed at a temperature of the catalyst in the range of from 300° C. to 600° C. using a gas stream comprising oxygen;
wherein the sequence of steps (a') to (c') in stage (i') performed n' times, where n' is an integer and at least 2, such that the washing of the catalyst with a liquid aqueous system according to step (c') is followed by the continuous preparation of propylene according to step (a') at least once without an intervening calcination stage (ii'); and
the process for the preparation of propylene oxide further comprising
(i") a stage comprising
(a") continuously preparing propylene oxide in a second reactor by a process comprising, in the following order:
(a1") introducing a feed stream comprising propene, hydrogen peroxide or a hydrogen peroxide source, and an organic solvent into the second reactor comprising a catalyst comprising a titanium comprising zeolite of MWW framework structure as catalytically active material;
(a2") subjecting the feed stream according to (a1") in the second reactor to epoxidation conditions in the presence of the catalyst, obtaining a reaction mixture comprising the propylene oxide and the organic solvent;
(a3") removing a product stream comprising the propylene oxide and the organic solvent from the second reactor;
(b") stopping introducing the feed stream into the second reactor; and
(c") washing the catalyst with a liquid aqueous system comprising at least 50 weight-% water, based on the total weight of the liquid aqueous system; and then
(ii") a stage comprising calcining the catalyst obtained from (c"), wherein the calcining is performed at a temperature of the catalyst in the range of from 300° C. to 600° C. using a gas stream comprising oxygen;
wherein the sequence of steps (a") to (c") in stage (i") is performed n" times, where n" is an integer and at least 1, such that the washing of the catalyst with a liquid aqueous system according to step (c") is followed by the continuous preparation of propylene according to step (a") at least once without an intervening calcination stage (ii"); and
wherein during at least one sequence of steps (b') and (c') in the first reactor or during at least one sequence of steps (b'), (c'), and (ii') in the first reactor, propylene oxide is prepared according to (a") in the second reactor.

18. The process of claim 17, further comprising:
repeating stages (i') and (ii') m' times, wherein m' is an integer and at least 1, and wherein in each repetition of stages (i') and (ii') the integer n' is the same or different; and/or
repeating stages (i") and (ii") m" times, wherein m" is an integer and at least 1, and wherein in each repetition of stages (i") and (ii") the integer n" is the same or different.

* * * * *

UNITED STATES PATENT AND TRADEMARK OFFICE
CERTIFICATE OF CORRECTION

PATENT NO. : 10,195,598 B2
APPLICATION NO. : 15/550581
DATED : February 5, 2019
INVENTOR(S) : Dominic Riedel et al.

Page 1 of 2

It is certified that error appears in the above-identified patent and that said Letters Patent is hereby corrected as shown below:

On the Title Page

Column 1, item (56), other publications, Line 14, "Zoelite" should read -- Zeolite --, In the Specification Column 6, Line 26, delete "1)($10^{-6}$:1" should read -- $1\times10^{-6}$:1 --, Column 12, Line 35, after "of" delete "of", Column 20, Line 3, "14:1;" should read -- 1.4:1; --, Column 20, Line 17, "methylpyrrolidini-um" should read -- methylpyrrolidinium --, Column 32, Line 51, "Kid" should read -- K/d --, Column 36, Line nos. 18-20, delete "Preferably, the washing in (c) is performed at a temperature of the liquid aqueous system in the range of from 30 to 20 90° C., preferably from 40 to 80° C." and insert the same on Column 36, Line 17, after "liquid aqueous system." as a continuation of the same paragraph, Column 43, Line 48, "emptied" should read -- emptied. --, Column 48, Line 14, "W." should read -- (I). --, Column 48, Line 56, "Kid." should read -- K/d. --, Column 49, Line 51, "S01)" should read -- S01,) --, Column 50, Line 24, "F)." should read -- E). --, Signed and Sealed this
Thirty-first Day of December, 2019

Andrei Iancu
*Director of the United States Patent and Trademark Office*

CERTIFICATE OF CORRECTION (continued)
U.S. Pat. No. 10,195,598 B2

Column 51, Line 21, "54)." should read -- S4). --,

Column 54, Line 43, "staffing" should read -- starting --,

Column 56, Line 35, "1-1202," should read -- $H_2O_2$, --.